United States Patent [19]

Emonds-Ai et al.

[11] Patent Number: 5,236,921
[45] Date of Patent: Aug. 17, 1993

[54] ARYLALKYLAMINES, PROCESS FOR PREPARING THEM AND PHARMACEUTICAL COMPOSITIONS CONTAINING THEM

[75] Inventors: Xavier Emonds-Ai, Combaillaux; Pierre Goulaouic, Montpellier; Vincenzo Proietto, Saint George D'Orques; Didier Van Broeck, Murviel les Montpellier, all of France

[73] Assignee: Sanofi, Paris, France

[21] Appl. No.: 755,454

[22] Filed: Sep. 5, 1991

[30] Foreign Application Priority Data

Sep. 5, 1990 [FR] France ................. 90 11039
Jun. 25, 1991 [FR] France ................. 91 07824

[51] Int. Cl.$^5$ ............... C07D 211/32; C07D 241/00; A01N 43/40
[52] U.S. Cl. ................... 514/252; 514/255; 514/318; 514/319; 514/323; 514/324; 514/327; 514/329; 514/330; 514/331; 544/336; 544/405; 544/408; 544/409; 546/193; 546/194; 546/201; 546/207; 546/208; 546/209; 546/214; 546/217; 546/221; 546/225; 546/228; 546/229; 546/231; 546/233; 546/331
[58] Field of Search ........... 546/234, 193, 194, 201, 546/207, 208, 209, 214, 231, 233, 217, 221, 225, 228, 229; 514/331, 252, 255, 318, 323, 324, 319, 329, 330; 544/333, 295, 298, 322, 334, 335, 336, 405, 408, 409

[56] References Cited

U.S. PATENT DOCUMENTS

| | | | |
|---|---|---|---|
| 3,103,516 | 9/1963 | Scmitt et al. | 260/294 |
| 4,751,327 | 6/1988 | Kazmaier et al. | 564/307 |
| 4,916,156 | 4/1990 | Moosé et al. | 514/510 |
| 4,920,116 | 4/1990 | Morgan, Jr. et al. | 514/210 |

FOREIGN PATENT DOCUMENTS

| | | |
|---|---|---|
| 701994 | 1/1988 | Belgium . |
| 0110869 | 6/1984 | European Pat. Off. . |
| 0126612 | 11/1984 | European Pat. Off. . |
| 0254545 | 1/1988 | European Pat. Off. . |
| 0261842 | 3/1988 | European Pat. Off. . |
| 0288352 | 10/1988 | European Pat. Off. . |
| 0325406 | 7/1989 | European Pat. Off. . |
| 0428434 | 5/1991 | European Pat. Off. . |
| 1112514 | 8/1961 | Fed. Rep. of Germany . |
| 2370723 | 11/1977 | France . |
| WO88/02362 | 4/1988 | PCT Int'l Appl. . |
| 8802362 | 4/1988 | World Int. Prop. O. . |

OTHER PUBLICATIONS

A. Donetti, el. Marazzi-Uberti: "Central Nervous System Activity of Ethyl 1-Naphthylalkylcarbamates", Journal of Medicinal Chemistry, vol. 13, No. 4, 1970, pp. 747-448.

Chemical Abstracts, vol. 109, No. 17, Oct. 23, 1988, p. 53, "A novel series of potent and selective agonists at the opioid kappa-receptor".

Chemical Abstracts, vol. 111, No. 3, Jul. 17, 1989, p. 47, "ICI 204448: a kappa-opioid agonist with limited access to the CNS".

Primary Examiner—C. Warren Ivy
Assistant Examiner—Raymond Covington
Attorney, Agent, or Firm—Foley & Lardner

[57] ABSTRACT

The invention relates to compounds of formula:

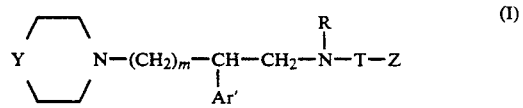

in which
Y represents—either a group Cy—N in which
  Cy represents a phenyl, optionally substituted; a $C_3-C_7$ cycloalkyl group; a pyrimidinyl group or a pyridyl group;
or a group

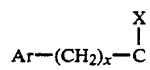

in which (Abstract continued on next page.)

Ar represents a phenyl, optionally substituted, a pyridyl group; a thienyl group;

x is zero or one;

X represents a hydroxyl, a $C_1$-$C_4$ alkoxy; a hydroxyalkyl; a $C_1$-$C_4$ acyloxy; a phenacyloxy; a carboxyl; a $C_1$-$C_4$ carbalkoxy; a cyano; an aminoalkylene; a group —N—$(X_1)_2$ in which the groups $X_1$ independently represent hydrogen, a $C_1$-$C_4$ alkyl; a group

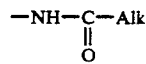

in which Alk represents a $C_1$-$C_6$ alkyl; a group

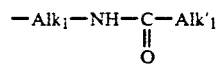

in which the $Alk_1$ is a $C_1$-$C_3$ alkylene and $Alk'_1$ is a $C_1$-$C_3$ alkyl; a $C_1$-$C_4$ acyl; a group —S—$X_2$ in which $X_2$ represents hydrogen or a $C_1$-$C_4$ alkyl group; or alternatively X forms a double bond with the carbon atom to which it is linked and with the adjacent carbon atom in the heterocycle;

m is 2 or 3;

Ar' represents a phenyl, optionally substituted; a thienyl; a benzothienyl; a naphthyl; an indolyl; an indolyl N-substituted with a $C_1$-$C_3$ alkyl;

R represents hydrogen, a $C_1$-$C_4$ alkyl;

T represents a group selected from —C(O)— and —C(W)—NH—

W being an oxygen or sulphur atom, and

Z represents either hydrogen, or M or OM when T represents a —C(O)— group, or M when T represents a group—C(W)—NH; M represents a $C_1$-$C_6$ alkyl; a phenylalkyl, a pyridyl alkyl; a naphthylalkyl; a pyridylthioalkyl; a styryl; or one of its salts with inorganic or organic acids.

18 Claims, No Drawings

ARYLALKYLAMINES, PROCESS FOR PREPARING THEM AND PHARMACEUTICAL COMPOSITIONS CONTAINING THEM

The present invention relates to new aromatic derivatives substituted with an amino group and with various ester, amine or amide functions The present invention also relates to the use of the compounds according to the invention in compositions for therapeutic application, and more especially in pathological phenomena involving the neurokinin system.

Endogenous ligands for neurokinin receptors have been described, such as substance P (SP), neurokinin A (NKA) (S. J. BAILEY et al., 1983, Substance P, P. Skrabanck ed., 16–17 Boole Press, Dublin) and neurokinin B (NKB) (S. P. WATSON, Life Sciences, 1983, 25, 797–808).

Neurokinin receptors have been recognised on numerous preparations, and are currently classified into three types: $NK_1$, $NK_2$ and $NK_3$. Whereas most preparations studied hitherto possess several types of receptors, such as guinea pig ileum ($NK_1$, $NK_2$ and $NK_3$), some of them appear to possess only one type, such as dog carotid artery ($NK_1$), rabbit pulmonary artery bereft of endothelium ($NK_2$) and rat portal vein ($NK_3$) (D. REGOLI et al., Trends Pharmacol. Sci., 1988, 9, 290–295 and Pharmacology, 1989, 38, 1–15).

A more precise characterisation of the different receptors is made possible by the recent synthesis of selective agonists. Thus, [$Sars^9$,Met—$(O_2)^{11}$]SP, [$Nle^{10}$]-$NKA_{4-10}$ and [Me $Phe^7$]NKB appear to exhibit a respective selectivity for $NK_1$, $NK_2$ and $NK_3$ receptors (see D. REGOLI, 1988 and 1989 cited above).

It has now been found that some aminated and variously substituted aromatic derivatives possess advantageous pharmacological properties as neurokinin A receptor antagonists, and are useful, in particular, for the treatment of any neurokinin A-dependent pathology.

The $NK_2$ receptor and neurokinin A are, for example, involved in neurogenic inflammations of the respiratory tract (P. J. BARNES, Arch. Int. Pharmacodyn., 1990, 303, 67–82 and G. F. JOOS et al., Arch. Int. Pharmacodyn., 1990, 303, 132–146).

To date, only peptide antagonists of $NK_2$ receptors have been described A publication by C. A. MAGGI et al., Br. J. Pharmacol., 1990, 100, 588–592, describes peptides which are selective antagonists of $NK_2$ receptors.

European Patent Application 0,347,802 describes peptide derivatives which are neurokinin A antagonists and useful as immunosuppressants in the treatment of arthritis, asthma, inflammation pain, gastrointestinal-hypermotility, Huntington's disease, psychoses, hypertension, migraine, urticaria and the like.

European Patent Application 0,336,230 also describes peptide derivatives which are substance P and neurokinin A antagonists and useful for the treatment and prevention of asthma.

Thus, according to one of its aspects, the present invention relates to variously substituted aromatic amino compounds of formula:

$$Y{-}N{-}(CH_2)_m{-}CH{-}CH_2{-}N(R){-}T{-}Z \quad (I)$$
$$\text{with substituent } Ar'$$

in which:

Y represents—either a group Cy—N in which
  Cy represents a phenyl, unsubstituted or substituted one or more times with one of the substituents selected from: hydrogen, a halogen atom, a hydroxyl, a $C_1$-$C_4$ alkoxy, a $C_1$-$C_4$ alkyl, a trifluoromethyl, the said substituents being identical or different; a $C_3$-$C_7$ cycloalkyl group; a pyrimidinyl group or a pyridyl group;

or a group $$Ar{-}(CH_2)_x{-}\overset{X}{C}$$

in which
  Ar represents a phenyl, unsubstituted or substituted one or more times with one of the substituents selected from: hydrogen, a halogen atom, a hydroxyl, a $C_1$-$C_4$ alkoxy, a trifluoromethyl, a $C_1$-$C_4$ alkyl, the said substituents being identical or different; a pyridyl group; a thienyl group;
  x is zero or one;
  X represents a hydroxyl, a $C_1$-$C_4$ alkoxy; a hydroxyalkyl in which the alkyl is a $C_1$-$C_3$ group; a $C_1$-$C_4$ acyloxy; a phenacyloxy; a carboxyl; a $C_1$-$C_4$ carbalkoxy; a cyano; an aminoalkylene in which the alkylene is a $C_1$-$C_3$ group; a group —N—$(X_1)_2$ in which the groups $X_1$ independently represent hydrogen, a $C_1$-$C_4$ alkyl; a group $$-NH-\underset{O}{\overset{\|}{C}}-Alk$$

in which Alk represents a $C_1$-$C_6$ alkyl; a group $$-Alk_1-NH-\underset{O}{\overset{\|}{C}}-Alk'_1$$

in which $Alk_1$ is a $C_1$-$C_3$ alkylene and $Alk'_1$ is a $C_1$-$C_3$alkyl; a $C_1$-$C_4$ acyl; a group —S—$X_2$ in which $X_2$ represents hydrogen or a $C_1$-$C_4$ alkyl group; or alternatively X forms a double bond with the carbon atom to which it is linked and with the adjacent carbon atom in the heterocycle;
  m is 2 or 3;
  Ar' represents a phenyl, unsubstituted or substituted one or more times with one of the substituents selected from: hydrogen, a halogen atom, preferably a chlorine or fluorine atom, a trifluoromethyl, a $C_1$-$C_4$ alkoxy, a $C_1$-$C_4$ alkyl, the said substituents being identical or different; a thienyl; a benzothienyl; a naphthyl; an indolyl; an indolyl N-substituted with a $C_1$-$C_3$ alkyl;
  R represents hydrogen, a $C_1$-$C_6$ alkyl;
  T represents a group selected from $$-\underset{O}{\overset{\|}{C}}- \text{ and } -\underset{O}{\overset{W}{\overset{\|}{C}}}-NH-$$

W being an oxygen or sulphur atom, and
Z represents either hydrogen, or M or OM when T represents a

group, or M when T represents a group

M represents a $C_1$-$C_6$ alkyl; a phenylalkyl in alkyl is a $C_1$-$C_3$ group, optionally substituted on the aromatic ring with a halogen, a trifluoromethyl, a $C_1$-$C_4$ alkyl, a hydroxyl, a $C_1$-$C_4$ alkoxy; a pyridylalkyl in which the alkyl is a $C_1$-$C_3$ group; a naphthylalkyl in which the alkyl is a $C_1$-$C_3$ group, optionally substituted on the naphthyl ring-system with a halogen, a trifluoromethyl, a $C_1$-$C_4$ alkyl, a hydroxyl, a $C_1$-$C_4$ alkoxy; a pyridylthioalkyl in which the alkyl is a $C_1$-$C_3$ group; a styryl; an optionally substituted mono-, di- or tricyclic aromatic or heteroaromatic group;
or one of its salts with inorganic or organic acids.

In the present description, the alkyl groups or alkoxy groups are linear or branched.

The salts of the compounds of formula (I) according to the present invention comprise both those with inorganic or organic acids which permit a suitable crystallisation or separation of the compounds of formula (I), such as picric acid or oxalic acid or an optically active acid, for example a mandelic or camphorsulphonic acid, and those which form pharmaceutically acceptable salts such as the hydrochloride, hydrobromide, sulphate, hydrogen sulphate, dihydrogen phosphate, methanesulphonate, methyl sulphate, maleate, fumarate, 2-naphthalenesulphonate, glycolate, gluconate, citrate or isethionate.

In particular, in the formula (I), Z represents a mono-, di- or tricyclic aromatic or heteroaromatic group, capable of bearing one or more substituents, in which a carbon atom of the aromatic carbocycle or aromatic heterocycle is linked directly to the group T.

More especially, the radical Z can be a phenyl group, which can be unsubstituted or optionally contain one or more substituents.

When Z is a phenyl group, the latter can preferably be mono- or disubstituted, in particular 2,4-disubstituted, but also, for example, 2,3-, 4,5-, 3,4- or 3,5- disubstituted; it can also be trisubstituted, in particular 2,4,6-trisubstituted, but also, for example, 2,3,4-, 2,3,5-, 2,4,5- or 3,4,5-trisubstituted; tetrasubstituted, for example 2,3,4,5-tetrasubstituted; or pentasubstituted. The substituents of the phenyl group can be: F;, Cl; Br; I, CN; OH; $NH_2$; NH—CO—$NH_2$; $NO_2$; $CONH_2$; $CF_3$; $C_1$-$C_{10}$ and preferably $C_1$-$C_4$ alkyl, methyl or ethyl being preferred, as well as, for example, n-propyl, isopropyl, n-butyl, isobutyl, sec-butyl, tert-butyl, pentyl or n-pentyl, hexyl or n-hexyl, heptyl or n-heptyl, octyl or n-octyl, nonyl or n-nonyl as well as decyl or n-decyl; alkenyl containing 2 to 10 and preferably 2-4 carbon atoms, for example vinyl, allyl, 1-propenyl, isopropenyl, butenyl or 1-buten-1-, -2-, -3- or -4-yl, 2-buten-1-yl, 2-buten-2-yl, pentenyl, hexenyl or decenyl; alkynyl containing 2 to 10 and preferably 2-4 carbon atoms, for example ethynyl, 1-propyn-1-yl, propargyl, butynyl or 2-butyn-1-yl, pentynyl, decynyl; cycloalkyl containing 3 to 8 and preferably 5 or 6 carbon atoms, cyclopentyl or cyclohexyl being preferred, as well as, for example, cyclopropyl, cyclobutyl, 1-, 2- or 3-methylcyclopentyl, 1-, 2-, 3- or 4-methylcyclohexyl, cycloheptyl or cyclooctyl, bicycloalkyl containing 4 to 11 and preferably 7 carbon atoms, exo- or endo-2-norbornyl being preferred, as well as, for example, 2-isobornyl or 5-camphyl; hydroxyalkyl containing 1 to 5 and preferably 1–2 carbon atoms, hydroxymethyl and 1- or 2-hydroxyethyl being preferred, as well as, for example, 1-hydroxy-1-propyl, 2-hydroxy-1-propyl, 3-hydroxy-1-propyl, 1-hydroxy-2-propyl, 1-hydroxy-1-butyl, 1-hydroxy-1-pentyl; alkoxy containing 1 to 10 and preferably 1–4 carbon atoms, methoxy or ethoxy being preferred, as well as, for example, n-propoxy, isopropoxy, n-butoxy, isobutoxy, sec-butoxy, tert-butoxy, pentyloxy, hexyloxy, heptyloxy, octyloxy, nonyloxy or decyloxy; alkoxyalkyl containing 2 to 10 and preferably from 2 to 6 carbon atoms, for example alkoxymethyl or alkoxyethyl such as methoxymethyl or 1- or 2-methoxyethyl, 1- or 2-n-butoxyethyl, 1- or 2-n-octyloxyethyl; alkoxyalkoxyalkyl containing up to 10 and preferably from 4 to 7 carbon atoms, for example alkoxyalkoxymethyl, for example 2-methoxyethoxymethyl, 2-ethoxyethoxymethyl or 2-isopropoxyethoxymethyl, alkoxyalkoxyethyl, for example 2-(2-methoxyethoxy)ethyl or 2-(2-ethoxyethoxy)ethyl; alkoxyalkoxy containing from 2 to 10 and preferably from 3 to 6 carbon atoms, for example 2-methoxyethoxy, 2-ethoxyethoxy or 2-n-butoxyethoxy; alkenyloxy containing 2 to 10 and preferably 2 to 4 carbon atoms, allyloxy being preferred, as well as, for example, vinyloxy, propenyloxy, isopropenyloxy, butenyloxy such as 1-buten-1-, -2-, -3- or -4-yloxy, 2-buten-1-yloxy, 2-buten-2-yloxy, pentenyloxy, hexenyloxy or decenyloxy; alkenyloxyalkyl with up to 10 and preferably 3–6 carbon atoms, for example allyloxymethyl; alkynyloxy containing from 2 to 10 and preferably from 2 to 4 carbon atoms, propargyloxy being preferred, as well as, for example, ethynyloxy, 1-propyn-1-yloxy, butynyloxy or 2-butyn-1-yloxy, pentynyloxy or decynyloxy; alkynyloxyalkyl containing from 3 to 10 and preferably 3 to 6 carbon atoms, for example ethynyloxymethyl, propargyloxymethyl or 2-(2-butyn-1-yloxy)ethyl; cycloalkoxy containing 3 to 8 and preferably 5 or 6 carbon atoms, cyclopentyloxy or cyclohexyloxy being preferred, as well as, for example, cyclopropyloxy, cyclobutyloxy, 1-, 2- or 3-methylcyclopentyloxy, 1-, 2-, 3- or 4-methylcyclohexyloxy, cycloheptyloxy or cyclooctyloxy; alkylthio containing from 1 to 10 and preferably 1 to 4 carbon atoms, methylthio or ethylthio being preferred, as well as, for example, n-propylthio, isopropylthio, n-butylthio, isobutylthio, sec-butylthio, tert-butylthio, pentylthio, hexylthio, octylthio, nonylthio or decylthio; alkylthioalkyl containing from 2 to 10 and preferably 2 to 6 carbon atoms, for example methylthiomethyl, 2-methylthioethyl or 2-n-butylthioethyl; acylamino, namely alkanoylamino containing from 1 to 7 and preferably 1 to 4 carbon atoms, formylamino and acetylamino being preferred, as well as propionylamino, butyrylamino, isobutyrylamino, valerylamino, caproylamino, heptanoylamino, as well as aroylamino or benzoylamino; acylaminoalkyl, preferably alkanoylaminoalkyl containing from 2 to 8 and preferably 3 to 6 carbon atoms, such as tormylaminoethyl, acetylaminoethyl, propionylaminoethyl, n-butyrylaminoethyl, formylaminopropyl, acetylaminopropyl, propionylaminopropyl, formylaminobutyl, acetylaminobutyl, as well as propionylaminobutyl, butyrylaminobutyl; acyloxy containing from 1 to 6 and preferably 2 to 4 carbon atoms, acetyloxy, propionyloxy or butyryloxy being preferred, as well as, for example, formyloxy, valeryloxy, caproyloxy; alkoxycarbonyl containing from 2 to 5 and preferably 2 and 3 carbon atoms, methoxycarbonyl and ethoxycarbonyl being preferred, as well as, for example, n-propoxycarbonyl, isopropoxycarbonyl, n-butoxycarbonyl, isobutoxycarbonyl, sec-butoxycarbonyl or tertbutoxycarbonyl; cycloalkoxycarbonyl containing from 4 to 8 and preferably 6 or 7 carbon atoms, cyclopentyloxycarbonyl, cyclohexyloxycarbonyl being preferred, as well as cyclopropyloxycarbonyl, cyclobutyloxycarbonyl or cycloheptyloxycarbonyl; alkylaminocarbonylamino containing from 2 to 4 carbon atoms, such as methylaminocarbonylamino, ethylaminocarbonylamino, propylaminocarbonylamino; dialkylaminocarbonylamino containing from 3 to 7 and preferably 3 to 5 carbon atoms, preferably dimethylaminocarbonylamino, as well as di-n-propylaminocarbonylamino, diisopropylaminocarbonylamino; pyrrolidinocarbonylamino; piperidinocarbonylamino; cycloalkylaminocarbonylamino containing from 4 to 8 and preferably 6 or 7 carbon atoms, cyclopentylaminocarbonylamino, cyclohexylaminocarbonylamino being preferred, as well as cyclopropylaminocarbonylamino, cyclobutylaminocarbonylamino, cycloheptylaminocarbonylamino; alkylaminocarbonylaminoalkyl containing from 3 to 9 and preferably 4 to 7 carbon atoms, methylaminocarbonylaminoethyl, ethylaminocarbonylaminoethyl, ethylaminocarbonylaminopropyl, ethylaminocarbonylaminobutyl being preferred, as well as, for example, methylaminocarbonylaminomethyl, n-propylaminocarbonylaminobutyl, n-butylaminocarbonylaminobutyl; dialkylaminocarbonylaminoalkyl containing from 4 to 11 carbon atoms, for example dimethylaminocarbonylaminomethyl, diethylaminocarbonylaminoethyl, diethylaminocarbonylaminopropyl, diethylaminocarbonylaminobutyl, pyrrolidinocarbonylaminoethyl, piperidinocarbonylaminoethyl; cycloalkylaminocarbonylaminoalkyl containing from 5 to 12 and preferably 8 to 11 carbon atoms, cyclopentylaminocarbonylaminoethyl, cyclopentylaminocarbonylaminopropyl, cyclopentylaminocarbonylaminobutyl, cyclohexylaminocarbonylaminoethyl, cyclohexylaminocarbonylaminopropyl and cyclohexylaminocarbonylaminobutyl being preferred, as well as, for example, cyclopropylaminocarbonylaminomethyl, cycloheptylaminocarbonylaminoethyl; alkoxycarbonylaminoalkyl containing from 3 to 12 and preferably 4 to 9 carbon atoms, methoxycarbonylaminoethyl, ethoxycarbonylaminoethyl, n-propoxycarbonylaminoethyl, isopropoxycarbonylaminoethyl, n-butoxycarbonylaminoethyl, isobutoxycarbonylaminoethyl, secbutoxycarbonylaminoethyl, tert-butoxycarbonylaminoethyl, ethoxycarbonylaminopropyl, n-butoxycarbonylaminopropyl, ethoxycarbonylaminobutyl, n-butoxycarbonylaminobutyl being preferred, as well as, for example, n-propoxycarbonylaminopropyl, n-propoxycarbonylaminobutyl, isopropoxycarbonylaminobutyl; cycloalkoxycarbonylaminoalkyl containing from 5 to 12 and preferably 8 to 11 carbon atoms, cyclopentyloxycarbonylaminoethyl, cyclopentyloxycarbonylaminopropyl, cyclopentyloxycarbonylaminobutyl, cyclohexyloxycarbonylaminoethyl, cyclohexyloxycarbonylaminopropyl, cyclohexyloxycarbonylaminobutyl being preferred, as well as, for example, cyclopropyloxycarbonylaminomethyl, cycloheptyloxycarbonylaminoethyl; carbamoylalkyl containing from 2 to 5 and preferably 2 carbon atoms, preferably carbamoylmethyl, as well as carbamoylethyl, carbamoylpropyl, carbamoylbutyl; alkylaminocarbonylalkyl containing from 3 to 9 and preferably 3 to 6 carbon atoms, methylaminocarbonylethyl, ethylaminocarbonylmethyl, n-propylaminocarbonylmethyl, isopropylaminocarbonylmethyl, n-butylaminocarbonylmethyl, isobutylaminocarbonylmethyl, sec-butylaminocarbonylmethyl, tert-butylaminocarbonylmethyl being preferred, as well as, for example, ethylaminocarbonylethyl, ethylaminocarbonylpropyl, ethylaminocarbonylbutyl, n-propylaminocarbonylbutyl, n-butylaminocarbonylbutyl; dialkylaminocarbonylalkyl containing from 4 to 11 and preferably 4 to 8 carbon atoms, dimethylaminocarbonylmethyl, diethylaminocarbonylmethyl, di-n-propylaminocarbonylmethyl, pyrrolidinocarbonylmethyl, piperidinocarbonylmethyl being preferred, as well as, for example, diethylaminocarbonylethyl, piperidinocarbonylethyl, diethylaminocarbonylpropyl, diethylaminocarbonylbutyl; cycloalkylaminocarbonylalkyl containing from 5 to 12 and preferably 7 or 8 carbon atoms, cyclopentylaminocarbonylmethyl and cyclohexylaminocarbonylmethyl being preferred, as well as, for example, cyclopropylaminocarbonylmethyl, cyclobutylaminocarbonylmethyl, cycloheptylaminocarbonylmethyl, cyclohexylaminocarbonylethyl, cyclohexylaminocarbonylpropyl, cyclohexylaminocarbonylbutyl; alkylaminocarbonylalkoxy containing from 3 to 10 and preferably 3 to 5 carbon atoms, methylaminocarbonylmethoxy being preferred, as well as, for example, methylaminocarbonylethoxy, methylaminocarbonylpropoxy; dialkylaminocarbonylalkoxy containing from 4 to 10 and preferably 4 to 7 carbon atoms, such as dimethylaminocarbonylmethoxy, diethylaminocarbonylethoxy, (1-piperidyl)carbonylmethoxy; cycloalkylaminocarbonylalkoxy containing from 5 to 11 and preferably 7 or 8 carbon atoms, such as cyclopentylaminocarbonylmethoxy, cyclohexylaminocarbonylmethoxy.

The radical Z can also represent a bicyclic aromatic group such as 1- or 2-naphthyl; 1-, 2-, 3-, 4-, 5-, 6-, 7-indenyl; in which one or more bonds may be hydrogenated, it being possible for the said groups to be unsubstituted or optionally to contain one or more substituents such as alkyl, phenyl, cyano, hydroxyalkyl, hydroxyl, oxo, alkylcarbonylamino, alkoxycarbonyl and thioalkyl groups, in which groups the alkyls are $C_1$-$C_4$ groups.

The radical Z can also be a pyridyl, thiadiazolyl, indolyl, indazolyl, imidazolyl, benzimidazolyl, quinolyl, benzotriazolyl, benzofuranyl, benzothienyl, benzothiazolyl, benzisothiazolyl, isoquinolyl, benzoxazolyl, benzisoxazolyl, benzoxazinyl, benzodioxinyl or pyridinyl, isoxazolyl, benzopyranyl, thiazolyl, thienyl, furyl, pyranyl, chromenyl, isobenzofuranyl, pyrrolyl, pyrazolyl, pyrazinyl, pyrimidinyl, pyridazinyl, indolizinyl, phthalazinyl, quinazolinyl, acridinyl, isothiazolyl, isochromanyl, chromanyl or carboxy aryl group, in which one or more double bonds may be hydrogenated, it being possible for the said groups to be unsubstituted or optionally to contain one or more substituents such as alkyl, phenyl, cyano, hydroxyalkyl, hydroxyl, alkylcarbonylamino, alkoxycarbonyl and thioalkyl groups, in which groups the alkyls are $C_1$-$C_4$ groups.

The group Z is preferably a phenyl group optionally disubstituted with a halogen, such as chlorine, or a thienyl group; the group T is preferably —C=O and the group R is preferably a methyl.

A group of preferred compounds of the invention is constituted by the compounds of formula (I) in which Ar', R, T, Z and m are as hereinabove defined and Y is a group of formula:

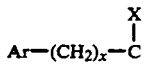

in which Ar and x are as hereinabove defined and X is a hydroxyl, an acetoxy or a group of formula:

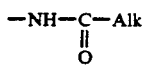

in which Alk represents a $C_1$-$C_6$ alkyl as their salts with organic or mineral acids.

A particularly preferred compound is N-methyl-N-[4-(4-phenyl-4-acetylamino-piperidyl)-2-(3,4-dichlorophenyl) butyl]benzamide under the racemic form or under the form of the enantiomers (+) or (−) as well as its salts with organic or mineral acids.

According to another of its aspects, the present invention relates to a process for the preparation of the compounds of formula (I) and its salts, characterised in that a) a free amine of formula:

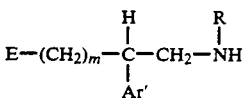   (II)

in which m, Ar' and R are as defined above and E represents an O-protecting group such as, for example, tetrahydro-2-pyranyloxy or a group

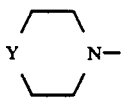

in which Y is defined as above, on the understanding that when Y represents a group

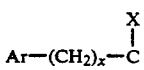

in which X is a hydroxyl, this hydroxyl may be protected; is treated either with a functional derivative of an acid of formula:

HO—CO—Z   (III)

in which Z is as defined above, when a compound of formula (I) in which T is —CO— is to be prepared, or with an iso(thio)cyanate of formula:

   (III')

in which W and Z are as defined above, when a compound of formula (I) in which T is —C(W)—NH— is to be prepared, to form the compound of formula:

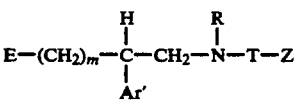   (IV)

b) then, when E represents tetrahydropyranyloxy, the tetrahydropyranyl group is removed by the action of an acid, c) the N-substituted alkanolamine thereby obtained, of formula:

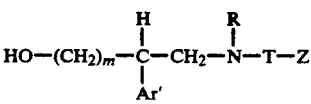   (V)

is treated with methanesulphonyl chloride d) the mesylate thereby obtained, of formula:

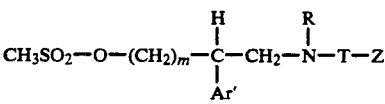   (VI)

is reacted with a secondary amine of formula:

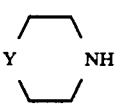   (VII)

in which Y is as defined above; and e) after deprotection, where appropriate, of the hydroxyl represented by X, the product thereby obtained is optionally converted to one of its salts.

As a functional derivative of the acid (III), the acid itself is used, suitably activated, for example, with cyclohexylcarbodiimide or with benzotriazolyl-N-oxy-tris(dimethylamino)phosphonium hexafluorophosphate (BOP), or alternatively with one of the functional derivatives which react with amines, for example an anhydride, a mixed anhydride, the acid chloride or an activated ester, is used. When Z is a group OM, the acid in question is carbonic acid, and the monochloride, namely a chloroformate Cl—CO—OM, is used as a functional derivative.

When a compound of formula (II) in which E represents a group

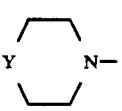

is used as starting material, the process of the present invention may be represented and illustrated in detail by Scheme 1 below:

SCHEME 1

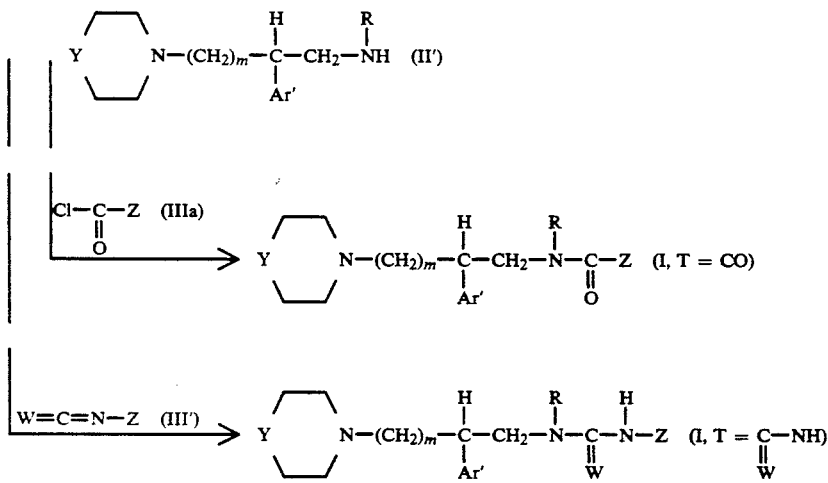

In the formula (IIIa) above, the acid chloride is considered to be the reactive functional derivative of the acid (III). It is possible, however, to use another functional derivative, or to start from the free acid (III), carrying out a coupling of (II') with BOP (benzotriazolyl-N-oxytris(dimethylamino)phosphonium hexafluorophosphate) and then adding the acid (III) in the presence of an organic base such as, for example, triethylamine, in a solvent such as dichloromethane or dimethylformamide, at room temperature; the compounds (I) obtained are isolated and purified according to the usual methods such as, for example, chromatography or recrystallisation.

It is also possible to react (II') with an iso(thio)cyanate W=C=N—Z (III') in an anhydrous inert solvent such as, for example, benzene, overnight at room temperature, and then to treat the reaction mixture according to the usual methods to obtain the compounds (I'').

When a compound of formula (II) in which E represents a tetrahydropyranyloxy group is used as starting material, the process of the present invention may be represented and illustrated using Scheme 2.

The reactions of the compound (II''') with the reagents (IIIa) and (III') proceed as described above for Scheme 1, it being possible for the acid chloride (IIIa) to be replaced by another functional derivative or by the free acid activated, for example, with BOP.

The intermediate (IV') thereby obtained is deprotected by mild acid hydrolysis to yield the free hydroxyl compound (V). The deprotection by hydrolysis of the tetrahydropyanyloxy group may also be carried out directly on the compound of formula (II''). Then, the hydroxylated compound of formula (II''') is obtained and it is directly reacted with the reagents (IIIa) or (III') as shown in the following scheme 2 to yield the compound of formula (V).

Starting from the compound of formula (V), the mesylate (VI) is prepared, the latter being substituted by a secondary amine of formula (VII) to obtain finally the compounds (I) according to the invention.

SCHEME 2

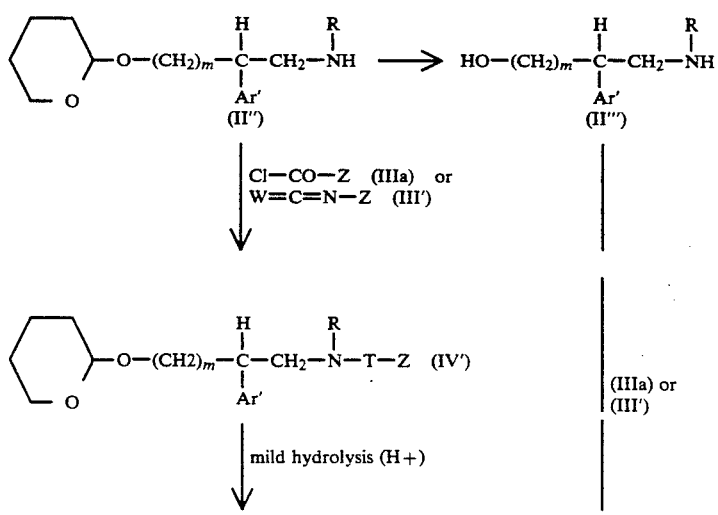

SCHEME 2

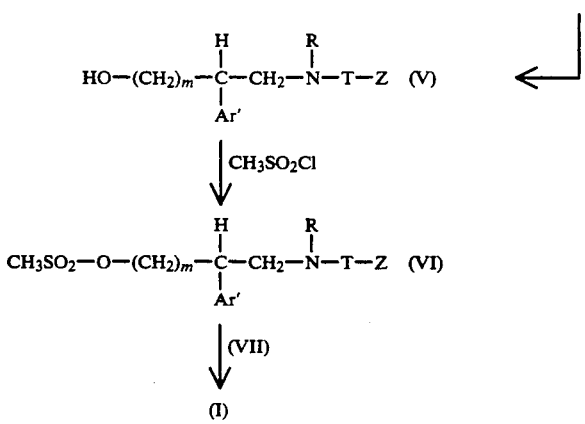

-continued

The products of formula (I) thereby obtained are isolated, in the form of a free base or salt, according to conventional techniques.

When the compound of formula (I) is obtained in the form of a free base, salification is performed by treatment with the selected acid in an organic solvent. By treatment of the free base, dissolved, for example, in an alcohol such as isopropanol, with a solution of the selected acid in the same solvent, the corresponding salt is obtained, which salt is isolated according to conventional techniques. Thus, the hydrochloride, hydrobromide, sulphate, hydrogen sulphate, dihydrogen phosphate, methanesulphonate, methyl sulphate, oxalate, maleate, fumarate or 2-naphthalenesulphonate, for example, is prepared.

At the end of the reaction, the compounds of formula (I) may be isolated in the form of one of their salts, for example the hydrochloride or oxalate; in this case, if necessary, the free base may be prepared by neutralisation of the said salt with an inorganic or organic base such as sodium hydroxide or triethylamine, or with an alkali metal carbonate or bicarbonate such as sodium or potassium carbonate or bicarbonate.

Resolution of the racemic mixtures and, where appropriate, mixtures of diastereoisomers (I) enables the enantiomers or diastereoisomers which form part of the invention to be isolated.

The resolution can also be carried out on the compounds of formula (II″) or (II‴) of above scheme 2, the following reactions in that scheme provoking no racemisation. Advantageously, the resolution is effected on a compound of formula (II‴) in which R is as hereinabove defined, preferably hydrogen. the separation is effected according to known methods by formation of a salt with an optically active acid, such as for example the D-(+) tartaric acid or the D-(−) tartaric acid, by separation of the diastereoisomer salts and hydrolysis. A compound particularly appropriate for the resolution is the compound of formula (II‴) in which R is hydrogen and Ar' is the 2,4- or 3,4-dichlorophenyl group.

The starting compounds of formula (II) are prepared from nitriles of formula

in which m, E and Ar' are as defined above, by reduction of the nitrile.

For the preparation of the compounds of formula (II) in which R is hydrogen, the starting nitriles of formula (VIII) are subjected to a hydrogenation in an alkanol such as ethanol, in the presence of a catalyst such as Raney nickel, and the free primary amine may be isolated according to conventional methods.

When it is desired to prepare the compounds of formula (II) in which R is a methyl group, the free amine, obtained by hydrogenation of the nitrile (VIII) as described above, is treated with a chloroformate, for example with the chloroformate of formula Cl—CO—OR$_1$, where R$_1$ is a C$_1$-C$_6$ alkyl, to obtain the carbamates of formula:

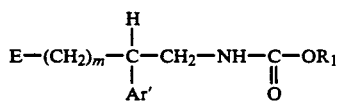

which are then reduced by known means such as the action of a reducing agent, for example a metal hydride such as sodium aluminium hydride or lithium aluminium hydride, or with a boron hydride such as borane dimethyl sulphide. The reduction is carried out in a solvent such as ether, toluene or tetrahydrofuran, at a temperature between room temperature and 60° C. The amine thereby obtained, of formula:

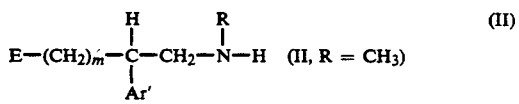

is isolated according to the usual methods.

It is also possible to treat the compound of formula:

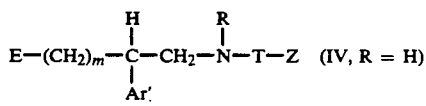

in which m, E, AR', T and Z are as defined above, with an alkyl halide in the presence of a strong base such as, for example, a metal hydride, for example sodium hydride, in an inert solvent such as tetrahydrofuran heated to reflux, to prepare the compounds (IV) in which R is other than hydrogen.

The nitriles of formula (VIII) are prepared from nitriles of formula:

Ar'—CH₂—CN (XI)

which, by alkylation with a compound of formula

E—(CH₂)ₘ—G (XII)

in which m and E are as defined above and G is a halogen atom, for example a bromine atom, or a protected hydroxyl group, give the desired compounds (VIII).

Synthesis of the nitriles of formula (VIII) in which E is a tetrahydropyranyloxy group is carried out from a tetrahydropyranyloxy (THP—O—) derivative obtained by reaction between an alkanol of formula Br—(CH₂)ₘ—OH, with m as defined above, and dihydropyran, to yield the compound

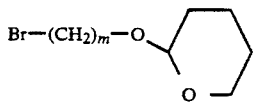

(XII, E = THP—O—, G = Br)

which is then added, in the presence of an alkali metal hydride, to the acetonitrile derivative (XI) to prepare the intermediate

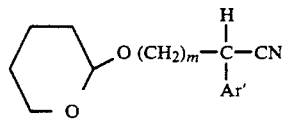

(VIII, E = THP—O—)

Synthesis of the nitriles of formula (VIII) in which E represents a group

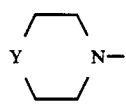

where Y is as defined above, is performed according to known methods by the addition to chlorinated derivatives of formula:

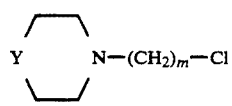

(XIII)

of a nitrile derivative of formula:

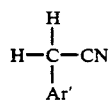

(XIV)

in the presence of sodium amide in a solvent such as toluene at temperatures of between 30° and 80° C.

The chlorinated derivative (XIII) is prepared by the action of a chlorinating reagent such as thionyl chloride on the hydroxyl derivative of formula:

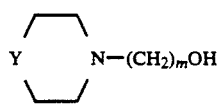

(XV)

which is itself prepared from the amine of formula (VII) in which, if X=OH, the hydroxyl group is then optionally protected with an O-protecting group, according to the usual methods,

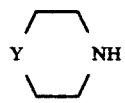

(VII)

which amine is reacted with ethylene oxide if m=2, and with a 3-halopropanol if m=3.

The compounds according to the invention were subjected to biochemical and pharmacological tests.

The antagonist properties with respect to binding to NK₂ receptors were demonstrated by tests carried out on rat duodenum membranes according to L. BERGSTOM et al., Mol. Pharmacol., 1987, 32, 764–771.

Tests were also carried out on rabbit pulmonary artery bereft of endothelium, which possesses NK₂ receptors whose activation leads to a muscle contraction. The tests on different isolated organs were carried out according to D. REGOLI et al., Trends Pharmacol. Sci., 1988, 9, 290–295 and Pharmacology, 1989, 38, 1–15.

Tests on bronchospasm in guineapigs induced by an NK₂ agonist were carried out according to H. KONZETT et al., Arch. Exp. Path. Pharm., 1940, 195, 71–4.

The compounds according to the invention displace [[2-$^{125}$I]histidyl]neurokinin A from its receptor with a Ki of the order of 3 to 0.50 nM.

The same compounds, in the tests carried out on rabbit pulmonary artery, showed a pA₂ of 10.4 to 9.

The same compounds, in the tests carried out on bronchospasm in guineapigs, showed an antagonist activity with respect to [Nle$^{10}$]neurokinin A when administered i.v. at a dose of 200 μg/kg.

In view of the antagonist properties with respect to neurokinin A with which the compounds according to the invention are endowed, they may be useful in any neurokinin A-dependent pathology, and more especially in neurogenic inflammations of the respiratory tract, such as, for example, asthma or bronchoconstriction.

The compounds of the present invention are of low toxicity; in particular, their acute toxicity is compatible with their use as a medicinal product. For such a use, an effective quantity of a compound of formula (I) or of one of its pharmaceutically acceptable salts is administered to mammals.

The compounds of the present invention are generally administered in the form of dosage units. The said dosage units are preferably formulated in pharmaceutical compositions in which the active principle is mixed with a pharmaceutical excipient.

Thus, according to another of its aspects, the present invention relates to pharmaceutical compositions containing as active principle a compound of formula (I) or one of its pharmaceutically acceptable salts.

In the pharmaceutical compositions of the present invention for oral, sublingual, subcutaneous, intramuscular, intravenous, transdermal, local or rectal administration, the active ingredients may be administered in single-dose administration forms, mixed with conventional pharmaceutical carriers, to animals and to human beings. Suitable single-dose administration forms comprise oral forms such as tablets, gelatin capsules, powders, granules and solutions or suspensions to be taken by mouth, forms for sublingual and buccal administration, forms for subcutaneous, intramuscular, intravenous, intranasal or intraocular administration, forms for rectal administration and forms for administration by inhalation or by application to the mucous membranes such as those of nose, throat or bronchi, for example using an aerosol containing the active principle in the form of a spray or a dry powder.

In order to obtain the desired effect, the dose of active principle can vary between 0.25 and 1000 mg per day, and preferably between 2 and 250 mg.

Each single dose can contain from 0.25 to 250 mg of active principle, and preferably from 1 to 125 mg, in combination with a pharmaceutical carrier. This single dose may be administered 1 to 4 times a day.

When a solid composition is prepared in the form of tablets, the active ingredient is mixed with a pharmaceutical vehicle such as gelatin, starch, lactose, magnesium stearate, talc, gum arabic or the like. The tablets may be coated with sucrose or other suitable substances, or alternatively treated in such a way that they have sustained or delayed activity and continuously release a predetermined quantity of active principle.

A preparation in the form of gelatin capsules is obtained by mixing the active ingredient with a diluent and pouring the mixture obtained into soft or hard gelatin capsules.

A preparation in the form of a syrup or elixir can contain the active ingredient together with a sweetener, preferably having zero energy content, and methylparaben and propylparaben as antiseptic, as well as an agent imparting flavour and a suitable colouring.

The water-dispersible powders or granules can contain the active ingredient mixed with dispersing agents or wetting agents or suspending agents such as polyvinylpyrrolidone, as well as with sweeteners or flavour correctors.

For rectal administration, suppositories which are prepared with binders melting at rectal temperature, for example cocoa butter or polyethylene glycols, are employed.

For parenteral, intranasal or intraocular administration, aqueous suspensions, isotonic saline solutions or sterile and injectable solutions which contain pharmacologically compatible dispersing agents and/or wetting agents, for example propylene glycol or butylene glycol, are used.

For administration by inhalation, an aerosol containing, for example, sorbitan trioleate or oleic acid, as well as trichlorofluoromethane, dichlorodifluoromethane, dichlorotetrafluoroethane or any other biologically compatible propellent gas, is used.

The active principle may also be formulated in the form of microcapsules, where appropriate with one or more carriers or additives.

The abovementioned compositions may also contain other active products such as, for example, bronchodilators, antitussives or antihistaminics.

The examples which follow illustrate the invention without, however, limiting it.

In the examples which follow, the following abbreviations have been used.

M.p.: instantaneous melting point expressed in degrees Celsius
Ac: Acetyl
AcO: Acetoxy The NMR spectra were recorded at 200 MHz in deuterated dimethyl sulphoxide.

up: unresolved peaks
s: singlet
bs: broad singlet
t: triplet
Mult: multiplet.

EXAMPLE 1

N-[2-(3,4-Dichlorophenyl)-4-(4-hydroxy-4-phenyl-piperidyl)butyl]-2,4-dichlorobenzamide hydrochloride

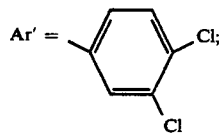

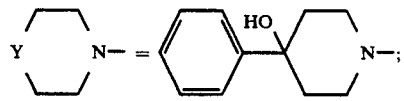

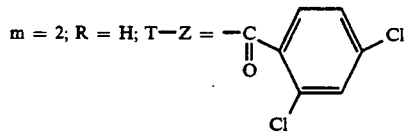

a)
α-(Tetrahydro-2-pyranyloxyethyl)-3,4-dichlorobenzeneacetonitrile 16.5 g of 80% sodium hydride in oil are suspended in 200 ml of dry tetrahydrofuran. A solution of 100 g of 3,4-dichlorobenzeneacetonitrile in 500 ml of tetrahydrofuran is added dropwise at 20° C. in the course of 30 minutes, and the reaction mixture is then stirred at room temperature for 2 hours. The mixture is cooled to −20° C. and a solution of 118 g of 1-bromotetrahydro-2-pyranyloxyethxnein in 100 ml of tetrahydrofuran is added, the mixture is allowed to return to room temperature and, after 2 hours, a solution of 50 g of ammonium chloride in 3 liters of water is added. The mixture is extracted with 1.5 liters of ether, and the organic phase is washed with saturated sodium chloride solution, separated after settling has taken place, dried over MgSO₄ and concentrated under vacuum.

The residue is chromatographed on silica gel; eluent: dichloromethane, then 95:5 (v/v) dichloromethane/ethyl acetate. The fractions of pure product are concentrated under vacuum to yield 118 g of an oil.

b)
β-(Tetrahydro-2-pyranyloxyethyl)-3,4-dichlorobenzeneethanamine 118 g of the nitrile obtained above are dissolved in 700 ml of absolute ethanol. 300 ml of concentrated ammonium solution are added and then, under a stream of nitrogen, Raney nickel (10% of the initial quantity of nitrile) is added. The mixture is then hydrogenated under a hydrogen atmosphere at room temperature and atmospheric pressure.

16 liters of hydrogen are absorbed in the course of 4 hours. The catalyst is separated by filtration on Celite, the filtrate is concentrated under vacuum and the residue is taken up in saturated sodium chloride solution. After extraction with ether and drying over MgSO₄, 112 g of an oil are obtained.

c)
N-[2-(3,4-Dichlorophenyl)-4-(tetrahydro-2-pyranyloxy)butyl]-2,4-dichlorobenzamide 80 g of the amine obtained above are dissolved in 800 ml of dichloromethane. The solution is cooled to 0° C. and 38.4 ml of triethylamine and then 55 g of 2,4-dichlorobenzoyl chloride are added. The reaction mixture is then stirred at room temperature for one hour and thereafter washed with water. The organic phase is separated after settling has taken place, dried over MgSO₄ and concentrated under vacuum to yield 120 g of an oil.

d)
N-[2-(3,4-Dichlorophenyl)-4-hydroxybutyl]-2,4-dichlorobenzamide 120 (9) of the product obtained above are dissolved in 1 liter of methanol in the presence of 12 g of paratoluenesulphonic acid. The reaction mixture is stirred for 18 hours at room temperature and then concentrated under vacuum. The residue is taken up in dichloromethane and washed with 10% sodium carbonate solution. The organic phase is separated after settling has taken place and dried over MgSO₄ to yield 106 g of an oil.

e)
N-[4-(Methanesulphonyloxy)-2-(3,4-dichlorophenyl)butyl]-2,4-dichlorobenzamide 106 g of the alcohol obtained above are dissolved in 1 l of dichloromethane, and 44 ml of triethylamine and 24.2 ml of methanesulphonyl chloride are then added to the solution cooled to 0° C. The reaction mixture is stirred at 0° C. for 45 minutes, washed 3 times with ice-cold water, separated after settling has taken place, dried over MgSO₄ and concentrated under vacuum. The residue is recrystallised from isopropyl ether.
m=95 g
M.p. 93° C.

f) Compound 1

A mixture of 1 g of the product obtained above, 0.8 g of 4-hydroxy-4-phenylpiperidine and 1 ml of dimethylformamide is heated to 60° C. for 2 hours. After cooling, it is diluted with ether and washed with dilute sodium hydroxide solution and then with water. After drying over MgSO₄, the solvents are evaporated off and the residue is chromatographed on 40 g of silica; elution: dichloromethane, then 90:10 (v/v) dichloromethane/methanol. Concentration of the pure fractions yields 0.9 g of the product, the hydrochloride of which is made in dichloromethane by adding ethereal hydrogen chloride to pH 1. The precipitate is separated by filtration and then solidified in ether.
m=0.95 g
NMR
8.75 (t, 1 H); 7.7–7 (up, 11 H); 5.4 (s, 1 H); 3.6–2.6 (up, 9 H); 2.6–1.6 (up, 6 H).

EXAMPLE 2
N-[2-(3,4-Dichloro)-4-(4-hydroxy-4-phenylpiperidyl)butyl]acetamide hydrochloride

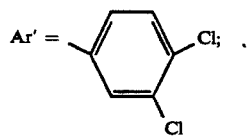

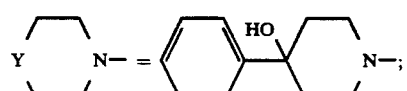

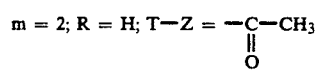

N-[2-(3,4-Dichlorophenyl)-4-mesyloxybutyl]-acetamide is prepared using the procedure described in Example 1 steps a), b), c), d) and e), replacing 2,4-dichlorobenzoyl chloride in step c) by acetyl chloride.

Compound 2

A mixture of 6.5 g of the product prepared above, 6.8 g of 4-hydroxy-4-phenylpiperidine and 10 ml of dimethylformamide is heated to 60° C.

After one hour, the reaction mixture is poured into water and extracted with ethyl acetate. The organic phase is separated after settling has taken place, dried over Na₂SO₄, filtered and concentrated under vacuum. The residue is purified by chromatography on silica gel; eluent: 10:90 (v/v) methanol/dichloromethane. Concentration of the fractions of pure product yields a residue which is salified with ethereal hydrogen chloride, and 6 g of hydrochloride are collected.
NMR
7.95 (t, 1 H); 7.7–7.0 (up, 8 H); 3.6–2.6 (up, 9 H); 2.6–1.3 (up, 9 H).

EXAMPLE 3
N-Ethyl-N-[2-(3,4-dichlorophenyl)-4-(4-hydroxy-4-phenylpiperidyl)butyl]-2-thiophenecarboxamide hydrochloride

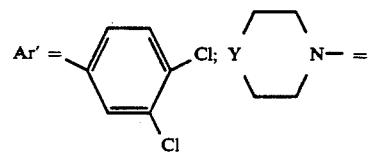

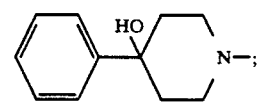

m = 2; R = —CH₂CH₃; T—Z = 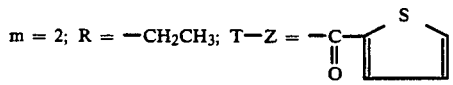

a)

N-Ethyl-β-[(4-hydroxy-4-phenylpiperidyl)ethyl]-3,4-dichlorobenzeneethanamine hydrochloride A solution of 5.5 g of Compound 2, obtained above, in 20 ml of tetrahydrofuran is added to a suspension of 0.96 g of lithium aluminium hydride in 10 ml of tetrahydrofuran, and the reaction mixture is heated to reflux for 2 hours. It is then cooled and hydrolysed with 4 ml of 4N sodium hydroxide solution, the alumina is filtered off and rinsed with tetrahydrofuran and the filtrate is evaporated. After salification with ethereal hydrogen chloride solution, the hydrochloride is solidified in an isopropanol/isopropyl ether mixture; 4.7 g are collected.

b) Compound 3

2.75 ml of triethylamine and then 0.8 g of 2-thenoyl chloride are added to a solution of 2.45 g of the product obtained above in dichloromethane at 0° C. After hydrolysis with 0.1N sodium hydroxide solution and extraction with dichloromethane, the product is purified by chromatography on silica H; eluent: 2.5:97.5 (v/v) methanol/dichloromethane. The pure product is salified with ethereal hydrogen chloride solution, and 1.0 g of hydrochloride is finally collected.

NMR 7.75–6.9 (up, 11 H); 5.35 (s, 1 H); 3.9–2.55 (up, 11 H); 2.55–1.5 (up, 6 H); 0.95 (t, 3 H)

EXAMPLE 4

N-Ethyl-N-[2-(3,4-dichlorophenyl)-4-(4-hydroxy-4-phenylpiperidyl)butyl]-4-methoxybenzamide hydrochloride Using the procedure of Example 3 step b), starting from the compound obtained in step a) and replacing 2-thenoyl chloride by 4-methoxybenzoyl chloride, Compound 4 is obtained.

M.p. 165° C.

EXAMPLE 5

N-{4-[4-Hydroxy-4-(2-pyridylmethyl)piperidyl]-2-(3,4-dichlorophenyl)butyl}-2,4-dichlorobenzamide dihydrochloride Ar' = 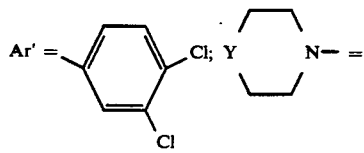 Cl; Y 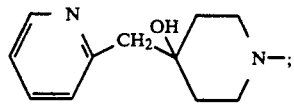 N— = m = 2; R = H; T—Z = 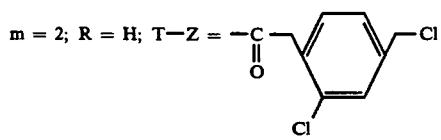

a)

N-[2-(3,4-Dichlorophenyl)-4-(4,4-ethylenedioxypiperidyl)butyl]-2,4-dichlorobenzamide A mixture of 12.1 g of the mesylate obtained in Example 1 e) and 8.6 g of 4,4-ethylenedioxypiperidine is heated to 100° C. for 15 minutes. The mixture is cooled, taken up in dichloromethane and washed with water. The organic phase is separated after settling has taken place, dried over Na₂SO₄, filtered and concentrated under vacuum. The residue is chromatographed on silica gel; eluent: 2:98 (v/v) methanol/dichloromethane.

Concentration of the pure fractions yields 12.15 g of expected product.

b)

N-[2-(3,4-Dichlorophenyl)-4-(4-oxopiperidyl)butyl]-2,4-dichlorobenzamide

The product obtained above is dissolved in 100 ml of acetone, and 100 ml of 6N hydrochloric acid are then added. After 2 hours, 1 liter of water and 1 liter of ether are added and the aqueous phase is recovered. The latter is then taken to pH 10 by adding sodium hydroxide and thereafter extracted with one liter of ether. After drying and evaporation of the organic phase, 9.7 g of pure product are obtained.

c) Compound 5

A 2.15M solution of 2-picolyllithium in tetrahydrofuran is added to a solution of 1 g of the product obtained above in 5 ml of tetrahydrofuran at 25° C. under nitrogen until the red coloration persists (see Synthesis page 43, 1974). After hydrolysis and extraction with ether, the residue is chromatographed on silica gel; eluent: 15:85 (v/v) methanol/dichloromethane. After evaporation of the pure fractions and salification of the residue with ethereal hydrogen chloride solution, 400 mg of a white foam are obtained.

NMR 8.8–7.15 (up, 11 H); 5.3 (broad s, 1 H); 4–2.55 (up, 11 H); 2.35–1.4 (up, 6 H).

EXAMPLE 6

N-[4-(4-Benzyl-4-hydroxypiperidyl)-2-(3,4-dichlorophenyl)butyl]-N'-(1-naphthyl)urea hydrochloride Ar' = 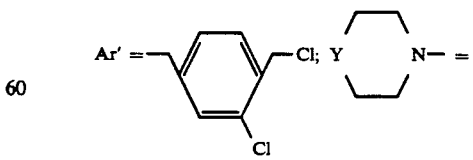 Cl; Y 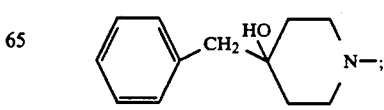 N— =

-continued m = 2; R = H; T—Z = 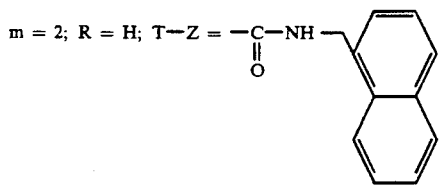

a) N-[4-(Tetrahydro-2- pyranyloxy)- 2 -(3,4-dichlorophenyl)butyl]-N'-(1-naphthyl)urea 12 g of β-(tetrahydro-2-pyranyloxyethyl)-3,4-dichlorobenzenethanamine in 50 ml of toluene are added to a solution of 7.6 g of 1-naphthyl isocyanate in 50 ml of toluene. After the reaction mixture has been stirred for 10 minutes, 50 ml of methanol are added and the mixture is concentrated under vacuum.

b) N-[4-Hydroxy-2-(3,4-dichlorophenyl)butyl]-N'-(1-naphthyl)urea 2 g of p-toluenesulphonic acid are added to a solution of the product obtained above, and the mixture is heated to reflux for 10 min. The solution is washed with sodium bicarbonate and concentrated to dryness. After purification of the residue by chromatography on silica gel, eluting with ethyl acetate, 13.1 g of a colourless oil are obtained.

c) N-[2-(3,4-Dichlorophenyl)-4-mesyloxybutyl]-N'-(1-naphthyl)urea 5.37 ml of triethylamine and then 2.77 ml of mesyl chloride are added at 0° C. to a solution of 13.1 g of the product obtained above in 100 ml of dichloromethane. The solution is then washed with 3 times 100 ml of ice-cold water and the organic phase is thereafter dried and evaporated. The residue is then recrystallised in isopropanol and thereafter filtered and rinsed with isopropyl ether.
m=8 g
M.p. 120° C.

d) Compound 6

A mixture of 4 g of product obtained above, 4 g of 4-hydroxy-4-benzylpiperidine and 4 ml of dimethylformamide is heated to 100° C. for 20 minutes. The whole is then poured into water and extracted with dichloromethane. The residue is then purified by chromatography on silica gel, eluting with a 4:96 (v/v) methanol/dichloromethane mixture. After salification with ethereal hydrogen chloride solution, 1.0 g of pure hydrochloride is collected.
NMR
8.7 (s, 1 H); 8.2–6.8 (up, 16 H); 3.5–2.5 (up, 11 H); 2.3–1.3 (up, 6 H).

The compounds described in Tables 1, 2 and 3 below were synthesised in the same manner as Examples 1 to 5. These compounds are all hydrochlorides.

TABLE 1

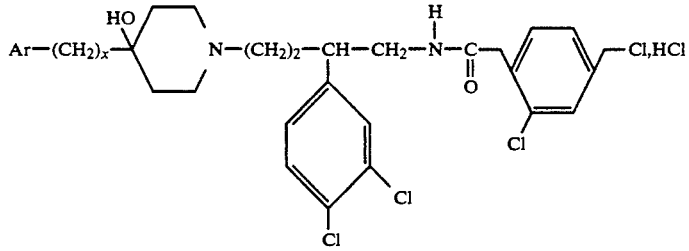

| Example No. | Ar | x | NMR spectrum |
|---|---|---|---|
| 7 | phenyl | 1 | 8.54(t, 1H); 7.7–7(up, 11H); 4.8(broad s 1H); 3.8–2.55(up, 11H); 2.4–1.25(up, 6H). |
| 8 | 4-chlorophenyl | 1 | 8.6(t, 1H); 7.8–7.2(up, 10H); 4.9(s, 1H); 3.7–2.6(up, 11H); 2.2–1.4(up, 6H). |
| 9 | 3-CF₃-phenyl | 0 | 8.55(t, 1H); 7.8–7.2(up, 10H); 5.70(s, 1H); 3.6–2.6(up, 9H); 2.6–1.6(up, 6H). |
| 10 | 4-pyridyl | 1 | 8.7(d, 2H); 8.45(t, 1H); 7.85 (d, 2H); 7.6–7(up, 6H); 5.3 (broad s, 1H); 4.0–2.3(up, 11H); 2.3–0.6(up, 6H). |

TABLE 2

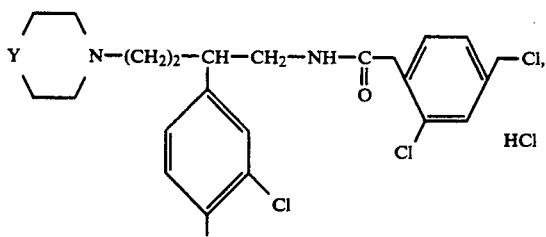

| Example No. | Y⟨N- | NMR spectrum |
|---|---|---|
| 11 | (pyrimidin-2-yl piperazine structure) | 8.4–8.8(up, 3H); 7.2–7.8(up, 6H); 6.8(t, 1H); 4.7(d, 2H); 2.6–3.8(up, 11H); 2.2(Mult., 2H). |

TABLE 3

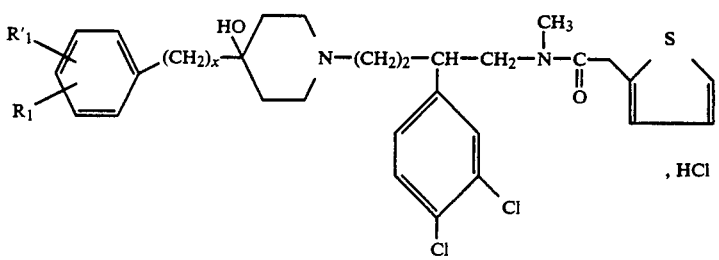

| Example No. | R₁ | R'₁ | x | NMR spectrum |
|---|---|---|---|---|
| 12 | H | H | 1 | 7.8–6.8(up, 11H); 4.75(s, 1H); 4.0–2.5(up, 14H); 2.3–1.3(up, 6H). |
| 13 | 4-OCH₃ | H | 0 | 6.9–7.4(up, 5H); 3.9–4.9(up, 1H); 0.6–2.6(up, 11H). |

EXAMPLE 14

N-Methyl-N-[2-(3,4-dichlorophenyl)-4-(4-hydroxy-4-phenylpiperidyl)butyl]benzamide hydrochloride

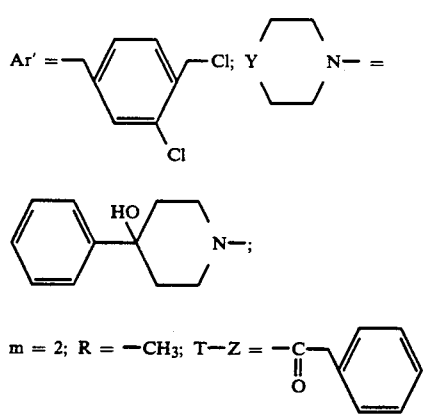

$m = 2$; $R = -CH_3$; $T-Z = -\overset{\underset{\|}{O}}{C}-\text{Ph}$ a) Ethyl N-[2-(3,4-dichlorophenyl)-4-(tetrahydro-2-pyranyloxy)butyl]carbamate 26.4 ml of ethyl chloroformate are added dropwise to a solution, cooled to −20° C., of 80 g of amine obtained in Example 1 b) and 39 ml of triethylamine in 800 ml of dichloromethane. After 30 minutes, the mixture is washed twice with water and then with a pH 2 buffer solution. The organic phase is separated after settling has taken place and dried over MgSO₄, then concentrated under vacuum to obtain 98 g of product in the form of an oil.

b) N-Methyl-β-[(tetrahydro-2-pyranyloxy)ethyl]-3,4-dichlorobenzeneethanamine 20 g of lithium aluminium hydride, suspended in 200 ml of tetrahydrofuran, are introduced into a 2-liter three-necked flask swept with nitrogen. A solution of 98 g of the carbamate obtained above in 800 ml of tetrahydrofuran is added at 20° C. .

The mixture is heated cautiously to reflux and the latter is maintained for 18 hours.

The mixture is cooled to 0° C. and hydrolysed with 35 ml of water and then with a mixture of 17 ml of concentrated sodium hydroxide solution and 150 ml of water. The inorganic matter is separated by filtration and the filtrate is then concentrated under vacuum to obtain 80.5 g of product in the form of an oil.

c) N-Methyl-β-hydroxyethyl-3,4-dichlorobenzeneethanamine hydrochloride 20 ml of concentrated hydrochloric acid are added to 50 g of protected amino alcohol obtained above, dissolved in 500 ml of ethanol. After 2 hours 30 minutes, the mixture is concentrated under vacuum, the residue is dissolved in 200 ml of acetonitrile, and 350 ml of ether are then added slowly. The mixture is stirred for one hour, and the crystals are filtered off and rinsed with ether.

m=32.8 g

M.p. 152° C.

d) tert-Butyl N-methyl-N-[2-(3,4-dichlorophenyl)-4-hydroxybutyl]-carbamate 20 ml of triethylamine are added to 32.8 g of hydrochloride of the above product, dissolved in 300 ml of dioxane and 30 ml of water. 27 g of Boc₂O (di-tert-butyl dicarbonate) are then added and the mixture is thereafter stirred at room temperature for 15 minutes. It is heated to 60° C. for 30 minutes. After concentration to dryness, the residue is taken up with ether and the organic phase is washed with water, then with a pH 2 buffer solution and then again with water. It is dried over MgSO₄ and concentrated under vacuum to obtain 40 g of oil.

e) tert-Butyl N-methyl-N-[2-(3,4-dichlorophenyl)-4-methanesulphonyloxybutyl]carbamate 17 ml of triethylamine are added to 40 g of the alcohol obtained above, dissolved in 400 ml of dichloromethane. The mixture is cooled to 0° C. and 9.3 ml of mesyl chloride are added dropwise. After 15 minutes, the mixture is washed twice with water, dried over MgSO₄ and concentrated to dryness to obtain 49 g of oil.

f) tert-Butyl N-methyl-N-[2-(3,4-dichlorophenyl)-4-(4-hydroxy-4-phenylpiperidyl)butyl]carbamate hydrochloride A mixture of 20 g of the product obtained above and 18 g of 4-hydroxy-4-phenylpiperidine in 40 ml of dimethylformamide is heated to 70° C. for 1 hour 30 minutes. The solution is then poured into 300 ml of ice-cold water and the precipitate is filtered off and rinsed with water. The solid is then taken up in ether and the organic phase is dried over MgSO₄ and evaporated. The crude product is purified by chromatography on silica gel, eluting with a gradient of methanol in dichloromethane (up to 5%). 22 g of pure product are obtained.

g) N-Methyl-β-[(4-hydroxy-4-phenylpiperidyl)ethyl]-3,4-dichlorobenzenemethanamine dihydrochloride 100 ml of concentrated hydrochloric acid and 20 ml of water are added to a solution of 22 g of the derivative obtained above in 100 ml of methanol. After one hour, the reaction mixture is concentrated under vacuum. A foam is obtained, which is ground in ether and then dried.

m=20.7 g h) Compound 14

0.51 ml of benzoyl chloride is added to a solution of 2 g of the product obtained above and 2 ml of triethylamine in 20 ml of dichloromethane at −78° C. under nitrogen, and the mixture is left stirring for 10 minutes. After hydrolysis with 0.1 N sodium hydroxide solution and extraction with dichloromethane, the product is purified by chromatography; eluent: 10:90 (v/v) methanol/dichloromethane. 1.37 g of pure product are thereby recovered, the hydrochloride of which product is made by adding ethereal hydrogen chloride to pH 1. 1.40 g of hydrochloride are finally obtained in the form of a foam.

NMR 7.7–6.6 (up, 13 H); 5.35 (s, 1 H); 3.8–2.5 (up, 12 H); 2.5–1.5 (up, 6 H).

EXAMPLE 15

N-Methyl-N-[2-(3,4-dichlorophenyl)-4-(4-hydroxy-4-phenylpiperidyl)butyl]-N'-benzylurea hydrochloride

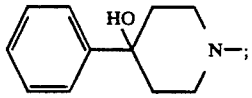

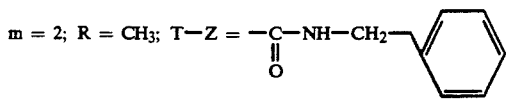

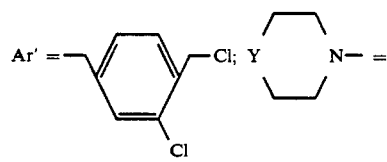

m = 2; R = CH₃; T—Z = —C—NH—CH₂—
                              ‖
                              O 0.60 ml of benzyl isocyanate is added to a solution of 2 g of the product obtained according to Example 14 g) and 1.2 ml of triethylamine in 20 ml of dichloromethane at 0° C. under nitrogen, and the mixture is left stirring for 1 hour. After washing with 0.1N sodium hydroxide solution, the product is purified by chromatography on silica gel; eluent: 6:94 (v/v) methanol/dichloromethane. The product is then salified with ethereal hydrogen chloride solution, and 1.8 g of hydrochloride are obtained.

NMR 7.7–6.9 (up, 13 H); 6.75 (t, 1 H); 5.4 (broad s, 1 H); 4.1 (up, 2H); 3.7–2.5 (up, 12 H); 2.5–1.4 (up, 6 H).

EXAMPLE 16

Ethyl N-methyl-N-[2-(3,4-dichlorophenyl)-4-(4-hydroxy-4-phenylpiperidyl)butyl]carbamate hydrochloride

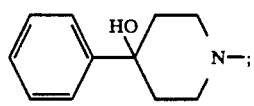

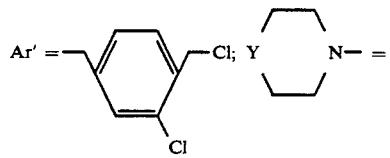

m = 2; R = —CH₃; T—Z = —C—OCH₂CH₃
                              ‖
                              O 0.44 ml of ethyl chloroformate is added to a solution of 2 g of product obtained above according to Example 14 g) and 2 ml of triethylamine in 20 ml of dichloromethane at −78° C. under nitrogen. After 5 minutes, the mixture is hydrolysed with 0.1N sodium hydroxide solution and extracted with dichloromethane. The product is then purified by chromatography on silica gel; eluent: 8:92 (v/v) methanol/dichloromethane. The pure fractions are concentrated under vacuum, and addition of ethereal hydrogen chloride enables 1.1 g of hydrochloride to be obtained in the form of a white foam.

NMR 7.7–7.1 (up, 8 H); 5.45 (s, 1 H); 4.1–2.6 (up, 14 H); 2.6–1.6 (up, 6 H); 1.1 (t, 3 H).

The compounds described in Tables 4 and 5 were synthesised according to Examples 14 to 16. These compounds are hydrochlorides.

TABLE 4

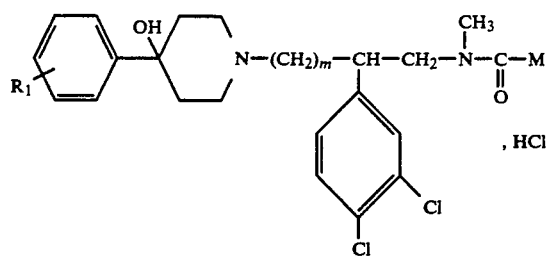, HCl

| ex. n° | M | R₁ | m | NMR spectrum or M.p., °C. |
|---|---|---|---|---|
| 17 | —CH₃ | H | 2 | 7.8–7.1(m, 8H); 3.7–2.65(m, 12H); 2.65–1.6(m, 9H). |
| 18 | —CH₂—CH₂—CH₃ | H | 2 | 7.7–7.0(m, 8H); 3.7–2.55(m, 12H); 2.55–0.5(m, 13H). |
| 19 | —CH(CH₃)₂ | H | 2 | 7.8–7.1(m, 8H); 5.5(s large, 1H); 3.9–2.65(m, 13H); 2.65–0.5(m, 12H). |
| 20 | —CH₂—C₆H₅ | H | 2 | 7.7–6.8(m, 13H); 5.35(s, 1H); 3.7–2.5(m, 14H); 2.5–1.5(m, 6H). |
| 21 | —C₆H₅ | 4-Cl | 2 | 7.8–6.9(m, 12H); 5.6(s, 1H); 3.9–2.6(m, 12H); 2.6–1.6(m, 6H). |
| 22 | —C₆H₅ | H | 3 | 148 |
| 23 | —CH₂—C₆H₅ | H | 2 | 198–200 |
| 24 | 4-methylthienyl | 4-CH₃ | 2 | 7.9–7.0(m, 10); 5.40(m, 1H); 3.9–2.6(m, 12H); 2.6–1.6(m, 9H). |
| 25 | thienyl | H | 2 | 7.9–6.5(m, 11H); 5.45(s, 1H); 3.9–2.6(m, 12H); 2.6–1.6(m, 6H). |
| 26 | furyl | H | 2 | 7.8–6.4(m, 11H); 5.3(s, 1H); 3.9–2.6(m, 12H); 2.4–1.6(m, 6H). |
| 27 | methylpyrrolyl | H | 2 | 7.6–7.2(m, 8H); 6.8(s, 1H); 6.4(s, 1H); 6.05(s, 1H); 5.4(s, 1H); 3.7(m, 2H); 3.4–2.6(m, 7H); 3.0(s, 3H); 2.4(m, 2H); 2.1(m, 2H); 1.7(m, 2H). |

TABLE 4-continued

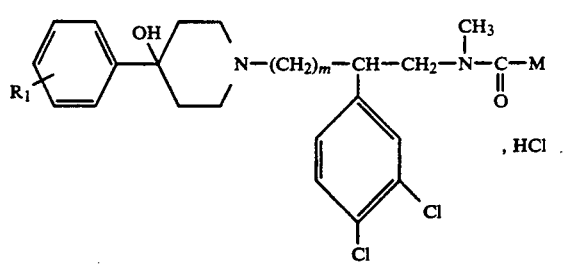, HCl

| ex. n° | M | R₁ | m | NMR spectrum or M.p., °C. |
|---|---|---|---|---|
| 28 | thiadiazolyl-methyl | H | 2 | 203 |
| 29 | 1-naphthyl | H | 2 | 198–200 |
| 30 | 4-fluoro-1-naphthyl | H | 2 | 180 (decomposition) |

TABLE 5

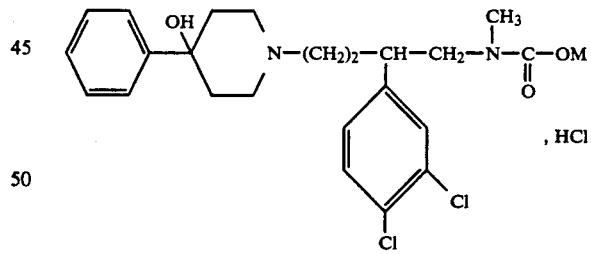, HCl

| example n° | M | NMR spectrum |
|---|---|---|
| 31 | —CH₂—C₆H₅ | 7.6–6.9(m, 13H); 5.35(s large, 1H); 5.1–4.6(m, 2H); 3.7–2.5(m, 12H); 2.5–1.5(m, 6H). |
| 32 | —C₆H₅ | 7.7–7.0(m, 11H); 6.85(d, J=8Hz, 1H); 6.75(d, J=8Hz, 1H); 5.35(s, 1H); 3.8–2.6(m, 12H); 2.4(m, 2H); 2.1(m, 2H); 1.7(m, 2H). |

EXAMPLE 33

N-[2-(3,4-Dichlorophenyl)-4-(4-hydroxy-4-phenyl-piperidyl)butyl]-N-methyl-2-thiophenecarboxamide hydrochloride

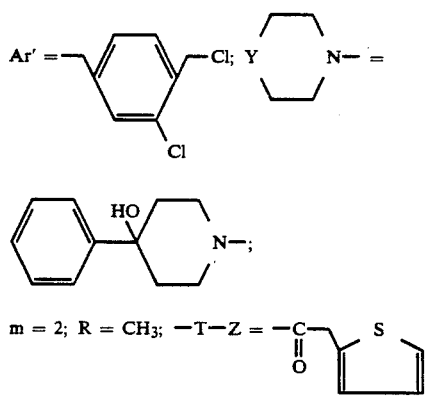

a)
N-[2-(3,4-Dichlorophenyl)-4-(tetrahydro-2-pyranyloxy)butyl]-2-thiophenecarboxamide A mixture of 4.77 g of amine obtained according to Example 1 b) and 1.7 g of triethylamine in 50 ml of dichloromethane is stirred at room temperature. 2.19 g of 2-thenoyl chloride, dissolved in 20 ml of dichloromethane, are then added dropwise at room temperature, and the mixture is left at room temperature overnight. The solvent is concentrated under vacuum, the residue is washed with water and the organic phase is extracted with ether and washed with 5% sodium bicarbonate solution and then with saturated sodium chloride solution; it is separated after settling has taken place, dried over Na$_2$SO$_4$, filtered and concentrated under vacuum. The residue is chromatographed on silica gel; eluent: 98:2 (v/v) methanol/dichloromethane. The pure fractions are collected and concentrated under vacuum. The residue is washed with 5% sodium hydroxide solution, extracted with ether and dried. 4.6 g of colourless oil are obtained.

b)
N-[2-(3,4-Dichlorophenyl)-4-(tetrahydro-2-pyranyloxy)butyl]-N-methyl-2-thiophenecarboxamide A mixture of 3.4 g of the amide obtained above and 0.45 g of 55% sodium hydride in 10 ml of tetrahydrofuran is stirred at room temperature. The reaction mixture becomes clear and orange in colour. 1.23 g of iodomethane in 10 ml of tetrahydrofuran are then added and the mixture is then stirred for 1 hour at room temperature and heated to reflux for 1 hour. The tetrahydrofuran is concentrated, the residue is taken up in water and extracted with ether and the organic phase is washed once again with water and with sodium chloride solution and concentrated under vacuum.
m=3.4 g c)
N-[2-(3,4-Dichlorophenyl)-4-hydroxybutyl]-N-methyl-2-thiophenecarboxamide 3.5 g of the product obtained above are dissolved in 30 ml of methanol in the presence of 0.35 g of resin (Amberlyst H-15, Aldrich, sulphonic acid resin, dry) and the mixture is heated to reflux for 1 hour 30 minutes.

The mixture is filtered on Celite, the filtrate is concentrated under vacuum and the residue is washed with hexane and then taken up in ether/hexane mixture. 2.6 g of white crystals are obtained.
M.p. 107°–109° C.

d)
N-[2-(3,4-Dichlorophenyl)-4-methanesulphonyloxybutyl]-N-methyl-2-thiophenecarboxamide.

2 g of alcohol obtained above and 0.65 g of triethylamine in 30 ml of dichloromethane are stirred at room temperature. A solution of 0.69 g of mesyl chloride in 10 ml of dichloromethane is then added dropwise. When the addition is complete, the mixture is heated to reflux for 30 minutes. The dichloromethane is evaporated off under vacuum, the residue is taken up with water and extracted with ethyl acetate, the organic phase is washed with 5% sodium bicarbonate solution and then with saturated sodium chloride solution and dried over Na$_2$SO$_4$ and the solvent is evaporated off.
m=1.2 g.

e) Compound 33

A mixture of 1 g of the product obtained above, 1 g of 4-hydroxy-4-phenylpiperidine and 2 ml of dimethylformamide is heated to 60° C. for 2 hours. After cooling, the mixture is diluted with ether and washed with water and then with dilute sodium hydroxide solution. It is dried over MgSO$_4$ and the solvents are then evaporated off. The residue is chromatographed on silica gel; eluent: dichloromethane to dichloromethane with the addition of 2.5% of methanol. 0.7 g of product is obtained, the hydrochloride of which product is made; after dissolution in dichloromethane, ethereal hydrogen chloride is added to pH 1 and the mixture is then concentrated under vacuum. The hydrochloride is solidified in ether.
m=0.74 g
NMR
7.8–6.8 (up, 11 H); 5.3 (s, 1 H); 3.8–2.5 (up, 12 H); 2.5–1.4 (up, 6 H).

The compounds described in Table 6 were prepared according to Example 33. These compounds are all hydrochlorides.

EXAMPLE 34

N-Methyl-N-{2-(3,4-dichlorophenyl)-4-[4-hydroxy-4-(4-hydroxyphenyl)piperidyl]butyl}-2-thiophenecarboxamide hydrochloride

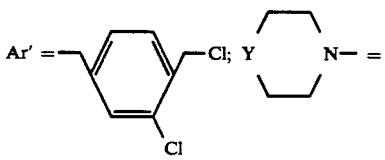

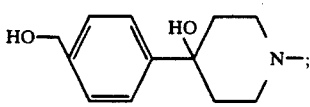

-continued m = 2; R = —CH₃; T—Z = 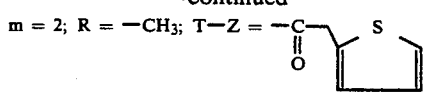

a) Preparation of the Amine:
4-hydroxy-4-(4-hydroxyphenyl)piperidine

Step 1

4-(Benzyloxy)bromobenzene 32.6 g of 4-bromophenol, 34.2 g of benzyl bromide and 42 g of potassium carbonate in 150 ml of dimethylformamide are stirred at 40° C. for 2 hours.

The solution is concentrated under vacuum, the residue is taken up in water and then extracted with ether and the organic phase is washed with water, separated after settling has taken place, dried over MgSO₄ and concentrated under vacuum.

The residue is recrystallised in isopropanol.
m=30 g
M.p. 61° C.
Step 2

1-Benzyl-4-(4-benzyloxyphenyl)-4-hydroxypiperidine 14 g of the product prepared above are dissolved in 100 ml of tetrahydrofuran and added to 1.2 g of magnesium recovered with 20 ml of tetrahydrofuran at 60° C. When the addition is complete, the temperature is maintained at 60° C. for 2 hours and the mixture is then cooled to −10° C. A solution of 10 g of 4-benzylpiperidone is then added dropwise and the mixture is allowed to return to room temperature. The mixture is poured into saturated ammonium chloride solution, the resulting mixture is extracted with ether and the organic phase is washed with water, separated after settling has taken place, dried over MgSO₄ and concentrated under vacuum. The residue is chromatographed on silica gel; eluent: 97.5:2.5 (v/v) dichloromethane/methanol. Concentration of the pure fractions yields 9 g of the expected product.
M.p.=104°–107° C.
Step 3

4-Hydroxy-4-(4-hydroxyphenyl)piperidine 6 g of the product obtained above, dissolved in 200 ml of ethanol, are hydrogenated at room temperature and atmospheric pressure in the presence of palladium on charcoal (10% Pd). When the theoretical volume of hydrogen is absorbed, the catalyst is filtered off, the filtrate is concentrated under vacuum, the residue is taken up with ether and the crystals are filtered off.
m=1.1 g
M.p. 232°–235° C.

b) Compound 34

2.1 g of the product obtained above according to Example 33 d), 1 g of the amine obtained in above step 3 and 1.1 g of triethylamine are dissolved in 5 ml of dimethylformamide and heated to 80° C. for 2 hours. The mixture is concentrated under vacuum, the residue is taken up in water and acidified to pH 3 with 6N hydrochloric acid solution, the mixture is extracted with ethyl acetate and the organic phase is separated after settling has taken place, dried over MgSO₄ and concentrated under vacuum.

The residue is taken up in acetone and solidified in ether.
m=0.7 g
NMR
9.3 (s, 1 H); 6.6–8 (up, 10 H); 5.2 (s, 1 H); 2.6–4 (up, 12 H); 1.6–2.4 (up, 6 H).

TABLE 6

| Example No. | Y | NMR spectrum |
|---|---|---|
| 35 | Cl-phenyl, HO, piperidine | 7.8–6.8(m, 10H); 5.5(s, 1H); 4.0–2.6(m, 12H); 2.6–1.5(m, 6H). |
| 36 | CF₃-phenyl, HO, piperidine | 8–7(m, 10H); 5.8(s, 1H); 4–2.7(m, 12H); 2.7–1.7(m, 6H). |
| 37 | Cl, CF₃-phenyl, HO, piperidine | 7.85(s, 1H); 7.75–7.2(m, 7H); 7.05(s, 1H); 5.8(s, 1H); 3.8–2.6(m, 12H); 2.6–1.6(m, 6H). |
| 38 | cyclohexyl-piperazine | 6.8–7.8(m, 6H); 2.6–4(m, 17H); 0.8–2.2(m, 12H). |
| 39 | phenyl-piperazine | 8.2(s, 2H); 6.7–7.8(m, 11H); 2–4 m, 18H). |
| 40 | (2-OCH₃-phenyl)-piperazine | 6.7–7.8(m, 10H); 1.8–4(m, 10H) |
| 41 | (CF₃-phenyl)-tetrahydropyridine | 7–8(m, 10H); 6.35(s, 1H); 2–4.2(m, 16H). |

EXAMPLE 42

N-[4-(4-Benzyl-4-acetyloxypiperidyl)-2-(3,4-dichlorophenyl)butyl]-2,4-dichlorobenzamide hydrochloride

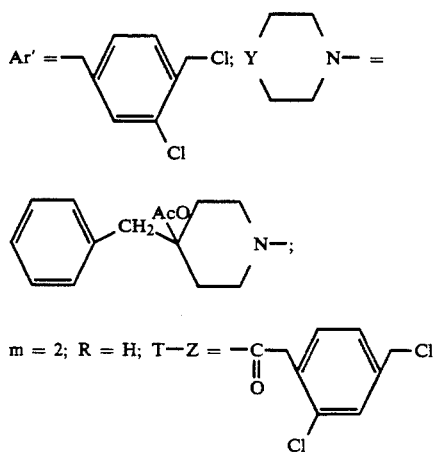

m = 2; R = H;

0.12 g of acetyl chloride is added to 0.4 g of N-[4-(4-benzyl-4-hydroxypiperidyl) -2-(3,4-dichlorophenyl)-butyl]-2,4-dichlorobenzamide hydrochloride (Compound 7), obtained according to Example 1, dissolved in 10 ml of dichloromethane in the presence of two equivalents of triethylamine.

After 1 hour's stirring at room temperature, the mixture is washed with water and the organic phase is separated after settling has taken place, dried over MgSO4 and concentrated under vacuum. The residue is chromatographed on silica gel; eluent: dichloromethane, then 95:5 (v/v) dichloromethane/methanol. The fractions of pure product are concentrated under vacuum, ethereal hydrogen chloride is then added to pH 1 and the ether is concentrated under vacuum.

The hydrochloride is solidified in ether.

m=0.26 g

NMR 8.5 (t, 1 H); 7.7–6.98 (up, 11 H); 3.6–2.6 (up, 11 H); 2.4–1.8 (up, 9 H).

The compounds described in Table 7 were prepared according to Examples 1 to 42.

TABLE 7

| Example No. | $R_1$ | X | NMR spectrum |
|---|---|---|---|
| 43 | H | —O—C(=O)—CH$_3$ | 7.9–6.9(up 11H); 4.0–2.65(up, 12H); 2.65–1.8(up, 9H). |
| 44 | 4-Cl | —O—C(=O)—CH$_3$ | 7.7–6.9(up, 10H); 3.8–2.5(up, 12H); 2.5–2.1(up, 6H); 2.0(s, 3H). |
| 45 | H | —CN | 7–7.9(up, 11H); 2–4.1(up, 18H). |
| 46 | H | —C(=O)—CH$_3$ | 7–7.8(up, 11H); 1.8–4(up, 21H). |
| 47 | H | —C(=O)—OCH$_2$CH$_3$ | 7–7.9(up, 11H); 2–4.3(up, 20H); 1.15(T, 3h). |

TABLE 8
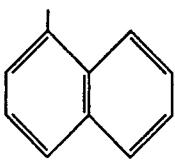
| Example No. | Ar' | —R | $Z_1$ | $Z_2$ | NMR spectrum or M.p., °C. |
|---|---|---|---|---|---|
| 48 | 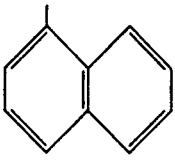 phenyl | $CH_3$ | H | H | 186 |
| 49 | naphthyl | H | H | H | 148–152 |
| 50 | naphthyl | $CH_3$ | H | H | 144–146 |
| 51 | naphthyl | H | $OCH_3$ | $OCH_3$ | 8.4(d, J=8Hz, 1H); 8.0–7.7(m, 4H); 7.7–7.2 (m, 8H); 6.6(m, 2H); 5.4(s, 1H); 4.1–2.8 (m, 9H); 3.8(s, 3H); 3.6(s, 3H); 2.5–2.2 (m, 4H); 1.8(m, 2H). |
| 52 | naphthyl | $CH_3$ | $OCH_3$ | $OCH_3$ | 140–145 (decomposition) |
| 53 | 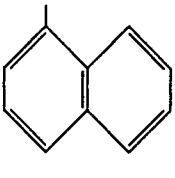 benzothienyl | $CH_3$ | H | H | 118 |
| 54 | 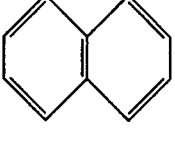 N-methylindolyl | $CH_3$ | H | H | 7.7–6.7(m, 15H); 5.4(m, 1H); 4.0–2.6 (m, 15H); 2.4–1.6(m, 6H) |

TABLE 9

[Structure: Y-N(piperazine/piperidine)-(CH₂)₂-CH(3,4-dichlorophenyl)-CH₂-N(CH₃)-C(=O)-CH₂-phenyl, HCl]

| Example n° | Y⟨N— (substituent) | NMR spectrum or M.p., °C |
|---|---|---|
| 55 | 4-(4-chlorophenyl)-4-acetoxy-piperidin-1-yl | 7.8–6.9 (m, 12H); 3.9–2.7 (m, 12H); 2.7–1.8 (m, 9H). |
| 56 | 4-(4-fluorophenyl)-4-hydroxy-piperidin-1-yl | 200 |
| 57 | 4-phenyl-4-(hydroxymethyl)-piperidin-1-yl | 7.8–6.8 (m, 13H); 4.6 (m, 1H); 3.8–1.8 (m, 20H). |
| 58 | 4-phenyl-4-ethoxy-piperidin-1-yl | 7.8–6.9 (m, 13H); 3.8–2.6 (m, 14H); 2.5–1.9 (m, 6H); 1.1 (t, J=6Hz, 3H). |
| 59 | 4-phenyl-4-acetoxy-piperidin-1-yl | 203 |
| 60 | 4-phenyl-4-propionyloxy-piperidin-1-yl | 198 |

TABLE 9-continued

[Structure: Y-N(piperazine/piperidine)-(CH₂)₂-CH(3,4-dichlorophenyl)-CH₂-N(CH₃)-C(=O)-CH₂-phenyl, HCl]

| Example n° | Y⟨N— (substituent) | NMR spectrum or M.p., °C |
|---|---|---|
| 61 | 4-phenyl-4-benzoyloxy-piperidin-1-yl | 140 |
| 62 | 4-phenyl-4-(aminomethyl)-piperidin-1-yl | 163 |
| 63 | 4-phenyl-4-(acetamidomethyl)-piperidin-1-yl | 144 |
| 64 | 4-(2-thienyl)-4-hydroxy-piperidin-1-yl | 188–190 |
| 65 | 4-(2-methoxyphenyl)-piperazin-1-yl | 134 |
| 66 | 4-(4-methoxyphenyl)-piperazin-1-yl | 114–116 |
| 67 | 4-(2-hydroxyphenyl)-piperazin-1-yl | 128–130 |

TABLE 10

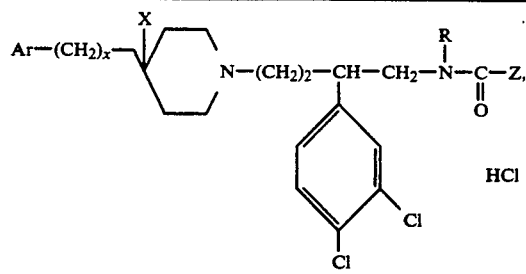

| Example n° | Ar—(CH₂)ₓ—C(X)(piperidine)N— | R | Z | M.p., °C. or NMR |
|---|---|---|---|---|
| 68 | benzyl-piperidine (X = H) | CH₃ | —CH₂—(3-chlorophenyl) | 7.7–6.8(m, 12H); 4.7(s, 1H); 3.6–2.4(m, 16H); 2.2–1.4(m, 6H). |
| 69 | 4-phenyl-4-cyano-piperidine | CH₃ | —CH₂—(3-chlorophenyl) | 7.7–6.8(m, 22H); 3.7–2.5(m, 14H); 2.6–2.0(m, 6H). |
| 70 | 4-phenyl-4-acetoxy-piperidine (OCOCH₃) | CH₃ | 2-naphthyl | 232 |

EXAMPLE 71

N-Methyl-N-[4-(4-phenyl-4-acetylaminopiperidyl)-2-(3,4-dichlorophenyl)butyl]benzamide hydrochloride A) Preparation of the amine: 4-Acetamido-4-phenyl-piperidine hydrochloride a) 4-Acetamido-4-phenyl-1-benzyl piperidine hydrochloride 260 ml of 95% sulphuric acid is added dropwise to 69 g of 1-benzyl-4-hydroxy-4-phenylpiperidine suspended in 300 ml of acetonitrile while the temperature is maintained at between 25° and 30° C. The reaction mixture is then stirred at room temperature for 4 hours and thereafter successively poured into ice and neutralised with 30% sodium hydroxide solution.

The precipitate is separated by filtration, washed with water and then dried in acetone.

m=58 g

M.p. 180.6°–182° C.

b) 4-Acetamido-4-phenylpiperidine hydrochloride

Ether saturated with hydrochloric acid is added to 58 g of the product prepared above, dissolved in 600 ml of methanol, to pH 1. The mixture is then hydrogenated at atmospheric pressure and room temperature in the presence of 6 g of palladium on charcoal (10% Pd). When the theoretical volume of hydrogen is absorbed, the catalyst is separated by filtration, the filtrate is concentrated under vacuum and the residue is recrystallised in ethanol.

m=45 g

M.p. 286.5°–288° C.

B) Preparation of Compound 71 a) N-[4-Methanesulphonyloxy-2-(3,4-dichlorophenyl)-butyl]-N-methylbenzamide

This compound is prepared according to Example 1, step e).

M.p. 100°–102° C.

b) Compound 71

1.4 g of 4-acetamido-4-phenylpiperidine and 1.4 g of the above mesylate are heated to 80° C. in 3 ml of DMF for 2 hours. Ice is added and the mixture is extracted with dichloromethane. The organic phase is separated after settling has taken place and washed successively water and then with saturated NaCl solution and dried over MgSO₄. It is concentrated under vacuum and the residue is chromatographed on silica gel; eluent: dichloromethane/methanol (97:3, v/v).

Concentration of the fractions of the pure product yields a residue which is taken up in methanol. The addition of ether saturated with hydrochloric acid yields the hydrochloride.

m=0.8 g

NMR: 3 H at 2

(s, CH₃—C—); 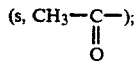
      ‖
      O

18 H between 2.10 and 3.90 (up, N—CH₃, all the CH₂, CH—C₆H₅; 13 H between 7.00 and 7.80 (up, aromatic H); 1 H at 8.20

(s, NH—C—). 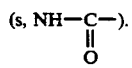
       ‖
       O

EXAMPLE 72

(−)-N-Methyl-N-[4-(4-phenyl-4-acetylaminopiperidyl)-2-(3,4-dichlorophenyl)butyl]benzamide hydrochloride Step 1

α-(Tetrahydro-2-pyranyloxyethyl)-3,4-dichlorobenzeneacetonitrile

This compound is prepared according to Example 1 a).

Step 2

β-(Tetrahydro-2-pyranyloxyethyl)-3,4-dichlorobenzeneethanamine

This compound is prepared according to Example 1b).

Step 3

β-Hydroxyethyl-3,4-dichlorobenzeneethanamine 81 g of the product obtained above according to step 2 are dissolved in 38 ml of methanol.

80 ml of saturated ethereal hydrogen chloride solution are added while the temperature is maintained at between 20° and 25° C. The mixture is stirred for 30 minutes at room temperature and then concentrated to dryness. The residue is dissolved in 250 ml of water and the solution is washed twice with ether, alkalinised with NaOH solution and extracted with dichloromethane. After drying over MgSO₄, the organic phase is concentrated to dryness, the residue is taken up in 800 ml of isopropyl ether, some insoluble matter is separated by filtration through Celite and the filtrate is concentrated under vacuum to approximately 300 ml, seeded with crystals of amino alcohol and stirred overnight.

The product is filtered off and rinsed with isopropyl ether and then with pentane. 30.2 g of the expected product are obtained.

M.p. 90°-91° C.

Step 4

(+)-β-Hydroxyethyl-3,4-dichlorobenzeneethanamine

A solution of 44.7 g of product obtained according to step 3 above in 300 ml of methanol is added to a boiling solution of 29 g of D-(−)-tartaric acid in 800 ml of methanol.

The mixture is allowed to return to room temperature and is stirred for 4 hours. It is filtered and the residue is rinsed with ethanol and then with ether. 34.1 g of tartrate are obtained.

The product is recrystallised in 1.75 l of methanol to obtain 26.6 g of tartrate.

$[\alpha]^{25}_D = -4.2$ (c=1, H₂O).

The tartrate is taken up in 120 ml of water. The mixture is alkalinised with NaOH solution and extracted twice with dichloromethane, and the organic phase is dried over MgSO₄ and concentrated to dryness. The residue is taken up in a little isopropyl ether, pentane is added and the mixture is filtered to obtain 15.4 g of product.

M.p. 79°-80° C.

$[\alpha]^{25}_D = +9.4$ (c=1, MeOH).

Step 5

Ethyl N-[4-hydroxy-2-(3,4-dichlorophenyl)butyl]carbamate 15 g of product obtained according to step 4 above are dissolved in 200 ml of dichloromethane. 9.9 ml of triethylamine are added.

The mixture is cooled to 0° C., and a solution of 6.3 ml of ethyl chloroformate in 30 ml of dichloromethane is added dropwise at this temperature. After 15 minutes, the mixture is washed with water, then with dilute HCl and then with saturated aqueous NaHCO₃ solution. After drying over MgSO₄, it is concentrated to dryness to obtain 20 g of product in the form of an oil.

Step 6

(+)-N-Methyl-β-hydroxyethyl-3,4-dichlorobenzeneethanamine hydrochloride

A solution of 20 g of product obtained according to step 5 above in 150 ml of anhydrous THF is added to 5.1 g of lithium aluminium hydride suspended in 60 ml of anhydrous THF. The mixture is heated to reflux for 1 hour. It is hydrolysed with 20 ml of water, the inorganic matter is filtered off and the filtrate is concentrated to dryness. The oil obtained is dissolved in 100 ml of acetone. Ether saturated with hydrochloric acid is added to pH 1, followed by ether until the mixture remains cloudy. The mixture is stirred for 1 hour and the crystals are filtered off and rinsed with a little acetone and then with a little ether to obtain 11 g of the expected product.

M.p. 129° C.

$[\alpha]^{25}_D = +8.4$ (c=1, MeOH).

Step 7

(−)-N-[4-Hydroxy-2-(3,4-dichlorophenyl)butyl]-N-methylbenzamine 8.4 ml of triethylamine are added to 8.1 g of product obtained according to step 6 above, suspended in 120 ml of dichloromethane. The mixture is cooled to 0° C. and a solution of 3.4 ml of benzoyl chloride in 35 ml of dichloromethane is added dropwise. After 15 minutes, the mixture is washed with water, then with dilute HCl and then with aqueous NaHCO₃ solution. It is dried over MgSO₄ and concentrated to dryness. A solid is obtained, which is taken up in ether and filtered off.

m=9.0 g

M.p. 129° C.

$[\alpha]^{25}_D = -19$ (c=1, MeOH).

Step 8

(−)-N-[4-Methanesulphonyloxy-2-(3,4-dichlorophenyl)butyl]-N-methylbenzamide 4.8 ml of triethylamine are added to 10.5 g of product obtained according to step 7 above, dissolved in 120 ml of dichloromethane. The mixture is cooled to 0° C. and 2.7 ml of methanesulphonyl chloride are added dropwise. After 15 minutes, the mixture is washed twice with water and then with saturated aqueous NaCl solution. It is dried over MgSO₄ and concentrated to dryness to obtain a foam.

$[\alpha]^{25}_D = -2.3$ (c=1, CHCl$_3$).

Step 9

Compound 72

22.7 g of 4-phenyl-4-acetylaminopiperidine hydrochloride are dissolved in 20 ml of water. 10 ml of concentrated sodium hydroxide solution are added. The mixture is extracted twice with dichloromethane and the organic phase is dried over MgSO$_4$. The solution obtained is added to the product obtained in step 8. The mixture is concentrated to dryness, 30 ml of DMF are added and the mixture is heated to 70° C. for 1 h 30 min. The solution is poured very slowly onto 30 ml of water+ice. The precipitate is filtered off, taken up several times in water and drained. It is purified by chromatography on silica; elution: pure dichloromethane, then dichloromethane with addition of methanol up to 10%.

Hydrochloride: The base is dissolved in acetone. Ether saturated with hydrochloric acid is added to pH 1. The solution is poured into isopropyl ether, the mixture is filtered and the product is dried.

m=11 g $[\alpha]^{25}_D = -29.5$ (c=1, MeOH).

NMR: 3 H at 1.85

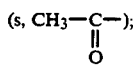

(s, CH$_3$—C—);
       ‖
       O

18 H between 2.0 and 3.75 (up, N—CH$_3$, all the CH$_2$, CH—C$_6$H$_5$); 13 H between 6.80 and 7.70 (up, aromatic H); 1 H at 8.10

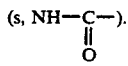

(s, NH—C—).
      ‖
      O

EXAMPLE 73

(+)-N-Methyl-N-[4-(4-phenyl-4-acetylaminopiperidyl)-2-(3,4-dichlorophenyl)butyl]benzamide hydrochloride The (+) enantiomer is prepared according to the same procedure as for the (−) enantiomer described in Example 41 above, replacing D-(−)-tartaric acid in step 4 by L-(+)-tartaric acid.

$[\alpha]^{25}_D = +30.6$ (c=1, MeOH).

NMR: 3 H at 1.85

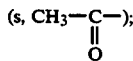

(s, CH$_3$—C—);
       ‖
       O

18 H between 2.00 and 3.75 (up, N—CH$_3$, all the CH$_2$, CH—C$_6$H$_5$); 13 H between 6.80 and 7.70 (up, aromatic H); 1 H at 8.10

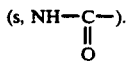

(s, NH—C—).
      ‖
      O

EXAMPLE 74

(−)-N-[2-(2,4-Dichlorophenyl)-4-(4-hydroxy-4-phenylpiperidyl)butyl]-N-methyl-2-thiophenecarboxamide hydrochloride This compound is prepared using the procedure of Example 72 above.

$[\alpha]^{25}_D = -51.0$ (c=1, MeOH).

EXAMPLE 75

(+)-N-[2-(2,4-Dichlorophenyl)-4-(4-hydroxy-4-phenylpiperidyl)butyl]-N-methyl-2-thiophenecarboxamide hydrochloride This compound is prepared using the procedure of Examples 72 and 73 above.

$[\alpha]^{25}_D = +52.7$ (c=1, MeOH).

The alcohols synthesised according to Example 1 d) above or according to Example 42 c) are key intermediates for the preparation of the compounds (I).

Table A below describes various alcohols which are useful for the preparation of compounds (I).

TABLE A

Synthesis intermediates

HO—CH$_2$—CH$_2$—CH—CH$_2$—N—C—M
                    |              |   ‖
                    |              R   O
                    |
                 (3,4-dichlorophenyl)

| Product No. | M | R | NMR spectrum |
|---|---|---|---|
| (a) | phenyl | CH$_3$ | 6.8–7.8(m, 8H); 4.5(se, 1H); 2.6–4(m, 8H); 1.3–2.1(m, 2H). |
| (b) | 2,6-dimethylphenyl | CH$_3$ | 6.8–7.6(m, 6H); 3–4.2(m, 5H); 2.4(s, 3H); 1.4–2.2(m, 8H). |
| (c) | 2-thienyl | CH$_3$ | 6.8–7.8(m, 6H); 4.4(t, 1H); 2.6–4(m, 8H); 1.4–1.9(se, 2H). |
| (d) | naphthyl | CH$_3$ | 1.3(m, 2H); 2.6–5(m, 9H); 8.2–6.2(m, 10H); 5–2.6(m, 9H); 1.3(m, 2H). |

We claim:

1. Compound of formula:

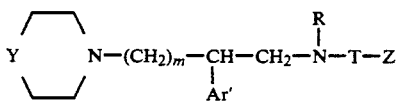 (I)

in which:
Y represents—either a group

in which
Cy represents a phenyl, unsubstituted or substituted one or more times with one of the substituents selected from: hydrogen, a halogen atom, a hydroxyl, a $C_1$-$C_4$ alkoxy, a $C_1$-$C_4$ alkyl, a trifluoromethyl, the said substituents being identical or different; a $C_3$-$C_7$ cycloalkyl group; a pyrimidinyl group or a pyridyl group;
or a group

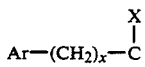

in which
Ar represents a phenyl, pyridyl or thienyl group, unsubstituted or substituted one or more times with one of the substituents selected from: hydrogen, a halogen atom, a hydroxyl, a $C_1$-$C_4$ alkoxy, the said substituents being identical or different, a trifluoromethyl, a $C_1$-$C_4$ alkyl, the said substituents being identical or different;
x is zero or one;
X represents a hydroxyl, a $C_1$-$C_4$ alkoxy; a hydroxyalkyl in which the alkyl is a $C_1$-$C_3$ group; a $C_1$-$C_4$ acyloxy; a phenacyloxy; a carboxyl; a $C_1$-$C_4$ carbalkoxy; a cyano; an aminoalkylene in which the alkylene is a $C_1$-$C_3$ group; a group —N—$(X_1)_2$ in which the groups $X_1$ independently represent hydrogen, a $C_1$-$C_4$ alkyl; a group

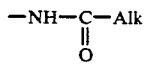

in which Alk represents a $C_1$-$C_6$ alkyl; a group

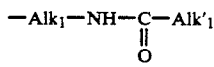

in which $Alk_1$ is a $C_1$-$C_3$ alkylene and $Alk'_1$ is a $C_1$-$C_3$ alkyl; a $C_1$-$C_4$ acyl; a group —S—$X_2$ in which $X_2$ represents hydrogen or a $C_1$-$C_4$ alkyl group; or alternatively X forms a double bond with the carbon atom to which it is linked and with the adjacent carbon atom in the heterocycle;
m is 2 or 3;
Ar' represents a phenyl, unsubstituted or substituted one or more times with one of the substituents selected from: hydrogen, a halogen atom, preferably a chlorine or fluorine atom, a trifluoromethyl, a $C_1$-$C_4$ alkoxy, a $C_1$-$C_4$ alkyl, the said substituents being identical or different; a thienyl; a benzothienyl; a naphthyl; an indolyl; an indolyl N-substituted with a $C_1$-$C_3$ alkyl;
R represents hydrogen, a $C_1$-$C_4$ alkyl;
T represents a group selected from

W being an oxygen or sulphur atom, and
Z represents either hydrogen, or M or OM when T represents a

group, or M when T represents a group

M represents a $C_1$-$C_6$ alkyl; a phenylalkyl in alkyl is a $C_1$-$C_3$ group, optionally substituted on the aromatic ring with a halogen, a trifluoromethyl, a $C_1$-$C_4$ alkyl, a hydroxyl, a $C_1$-$C_4$ alkoxy; a pyridyl alkyl in which the alkyl is a $C_1$-$C_3$ group; a naphthylalkyl in which the alkyl is a $C_1$-$C_3$ group, optionally substituted on the naphthyl ring-system with a halogen, a trifluoromethyl, a $C_1$-$C_3$ alkyl, a hydroxyl, a $C_1$-$C_4$ alkoxy; a pyridylthioalkyl in which the alkyl is a $C_1$-$C_3$ group; a styryl; an optionally substituted mono-, di- or tricyclic aromatic or heteroaromatic group; or one of its salts with inorganic or organic acids.

2. Compound according to claim 1 in which Ar' is a 3,4-dichlorophenyl group, or one of its salts with inorganic or organic acids.

3. Compound according to claim 1 in which X is a hydroxyl, an acetyloxy or a group

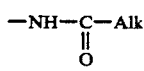

in which Alk represents a $C_1$-$C_6$ alkyl, or one of its salts with inorganic or organic acids.

4. Compound according to claim 1 in which R is a methyl, or one of its inorganic or organic salts.

5. Compound according to claim 1 in which T is a —C=O group, or one of its inorganic or organic salts.

6. Compound according to claim 1 in which T is a —C=O group and Z is a thienyl group, or one of its inorganic or organic salts.

7. Compound according to claim 1 in which T is a —C=O group and Z a phenyl group optionally disubstituted with a halogen such as chlorine, or one of its inorganic or organic salts.

8. Compound according to claim 1, which is N-methyl-N-[4-(4-phenyl-4-acetylamino-piperidyl)-2-(3,4-dichlorophenyl)butyl]benzamide under the racemic form or under the form of the enantiomers (+) or (−) and its salts with organic or mineral acids.

9. A compound according to claim 8, which is (−)-N-Methyl-N-[4-(4-phenyl-4-acetylamino piperidyl)-2-(3,4- dichlorophenyl)butyl]benzamide and its salts with organic or mineral acids.

10. A compound according to claim 8 which is (+)-N-Methyl-N-[4-(4-phenyl-4-acetylamino piperidyl)-2-(3,4-dichlorophenyl)butyl]benzamide and its salts with organic or mineral acids.

11. Pharmaceutical composition containing as active principle a compound of formula (I) according to claim 1.

12. Pharmaceutical composition according to claim 11, in the form of a dosage unit, in which the active principle is mixed with at least one pharmaceutical excipient.

13. A compound according to claim 1, wherein Y is $$Ar-(CH_2)_x-\underset{\diagdown}{\overset{X}{\underset{|}{C}}}\diagup$$

in which Ar is phenyl, X is —NH—CO—CH$_3$ and x is zero.

14. A compound according to claim 1, wherein Y is $$Ar-(CH_2)_x-\underset{\diagdown}{\overset{X}{\underset{|}{C}}}\diagup$$

in which Ar is phenyl, x is zero and X is a hydroxyl, an acetyloxy or a group —NH—CO—Alk in which Alk represents a C$_1$–C$_6$ alkyl, or a salt thereof with a pharmaceutically acceptable inorganic or organic acid.

15. A pharmaceutical composition according to claim 11, comprising as an active principle (−)-N-Methyl-N-[4-(4-phenyl-4-acetylamino piperidyl)-2-(3,4-dichlorophenyl)butyl]benzamide or a salt thereof with a pharmaceutically acceptable organic or mineral acid; and a pharmaceutically acceptable carrier.

16. Pharmaceutical composition according to claim 11, comprising as an active principle (+)-N-Methyl-N-[4-(4-phenyl-4-acetylamino piperidyl)-2-(3,4-dichlorophneyl)butyl]benzamide or a salt thereof with a pharmaceutically acceptable organic or mineral acid; and a pharmaceutically acceptable carrier.

17. A method for treatment of neurogenic inflammation of the respiratory tract, comprising the step of administering, to a patient in need of such treatment, a composition as recited in claim 11, in a therapeutic amount sufficient to displace neurokinin A from its receptors.

18. A method for treatment of neurogenic inflammation of the respiratory tract as recited in claim 18, wherein said therapeutic amount is about 0.25 to 100 mg per day of said compound according to formula (I).

* * * * *

UNITED STATES PATENT AND TRADEMARK OFFICE
CERTIFICATE OF CORRECTION

PATENT NO. : 5,236,921
DATED : August 17, 1993
INVENTOR(S) : Emonds-Alt, et. al.

It is certified that error appears in the above-indentified patent and that said Letters Patent is hereby corrected as shown below:

On the Title page, item [19] and [75], inventor: delete "Emonds-Ai" and insert -- Emonds-Alt--.

Signed and Sealed this

Eleventh Day of October, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,236,921
DATED : August 17, 1993
INVENTOR(S) : Emonds-Alt et al.

Page 1 of 10

It is certified that error appears in the above-indentified patent and that said Letters Patent is hereby corrected as shown below:

Column 20, lines 1-8, should read as follows:

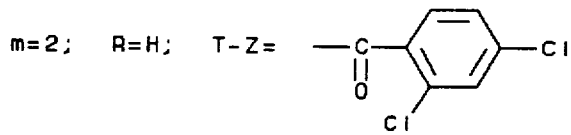

line 60, the formula for Ar' should read as follows:

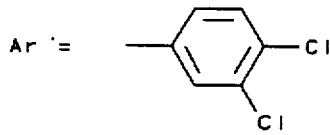

Column 21, lines 1-9, should read as follows:

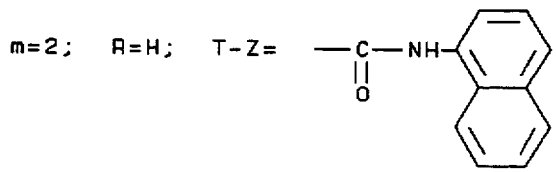

UNITED STATES PATENT AND TRADEMARK OFFICE
CERTIFICATE OF CORRECTION

PATENT NO. : 5,236,921                                       Page 2 of 10
DATED      : August 17, 1993
INVENTOR(S) : Emonds-Alt et al.

It is certified that error appears in the above-indentified patent and that said Letters Patent is hereby corrected as shown below:

Column 22,    line 32, the formula in Table 1 should read as follows:

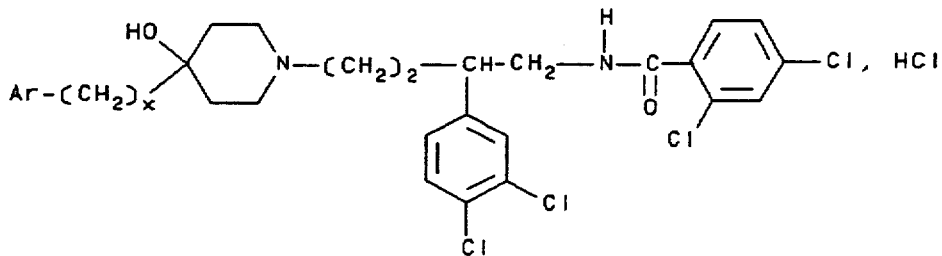

Column 23,    lines 1-8 should read as follows:

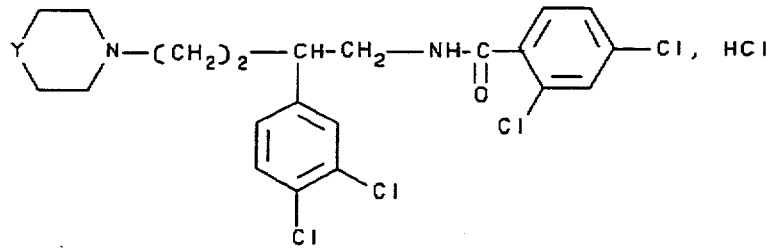

line 23, the formula in Table 3 should read as follows:

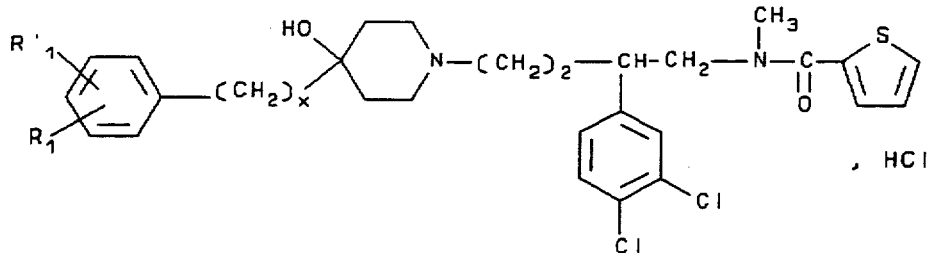

UNITED STATES PATENT AND TRADEMARK OFFICE
CERTIFICATE OF CORRECTION

PATENT NO. : 5,236,921
DATED : August 17, 1993
INVENTOR(S) : Emonds-Alt et al.

It is certified that error appears in the above-indentified patent and that said Letters Patent is hereby corrected as shown below:

line 46, the formula for Ar' should read as follows:

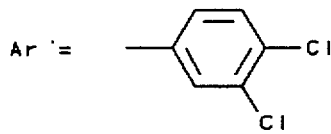

lines 56-60 should read as follows:

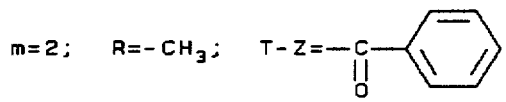

Column 25, lines 61, the formula for Ar' should read as follows:

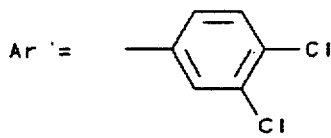

Column 26, lines 9-11 should read as follows:

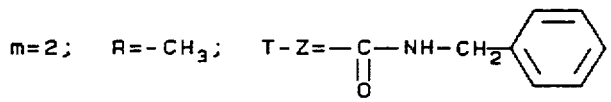

UNITED STATES PATENT AND TRADEMARK OFFICE
CERTIFICATE OF CORRECTION

PATENT NO. : 5,236,921
DATED : August 17, 1993
INVENTOR(S) : Emonds-Alt et al.

It is certified that error appears in the above-identified patent and that said Letters Patent is hereby corrected as shown below:

line 35, the formula for Ar' should read as follows:

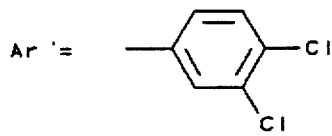

Column 27, line 28, the formula for Example 20 should read as follows:

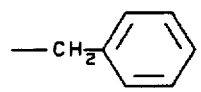

line 38, the formula for Example 22 should read as follows:

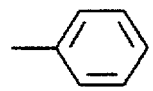

line 43, the formula for Example 23 should read as follows:

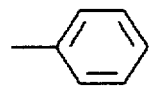

line 52, the formula for Example 25 should read as follows:

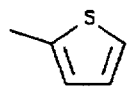

UNITED STATES PATENT AND TRADEMARK OFFICE
CERTIFICATE OF CORRECTION

PATENT NO. : 5,236,921
DATED : August 17, 1993
INVENTOR(S) : Emonds-Alt et al.

It is certified that error appears in the above-indentified patent and that said Letters Patent is hereby corrected as shown below:

Column 28, line 57, the formula for Example 31 should read as follows:

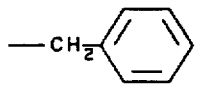

Column 29, line 9, the formula for Ar' should read as follows:

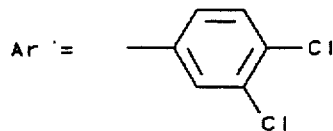

lines 19-21 should read as follows:

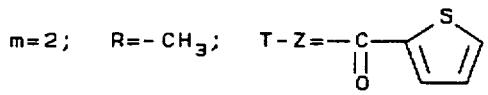

Column 30, line 58, the formula for Ar' should read as follows:

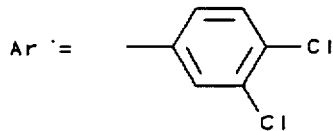

UNITED STATES PATENT AND TRADEMARK OFFICE
CERTIFICATE OF CORRECTION

PATENT NO. : 5,236,921

DATED : August 17, 1993

INVENTOR(S) : Emonds-Alt et al.

It is certified that error appears in the above-indentified patent and that said Letters Patent is hereby corrected as shown below:

lines 64-67 should read as follows:

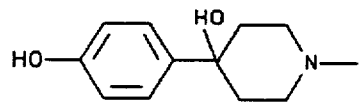

Column 31, lines 1-5 should read as follows:

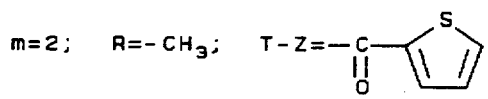

Column 32, lines 10-20 should read as follows:

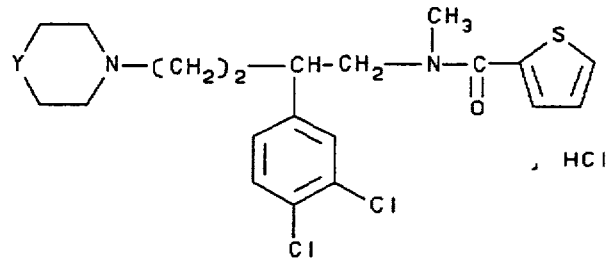

UNITED STATES PATENT AND TRADEMARK OFFICE
CERTIFICATE OF CORRECTION

PATENT NO. : 5,236,921
DATED : August 17, 1993
INVENTOR(S) : Emonds-Alt et al.

It is certified that error appears in the above-indentified patent and that said Letters Patent is hereby corrected as shown below:

Column 33, line 7, the formula for Ar' should read as follows:

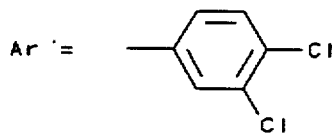

lines 19-22 should read as follows:

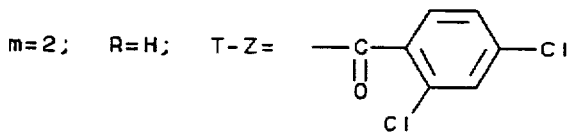

Column 34, the formula at the top of Table 7 should read as follows:

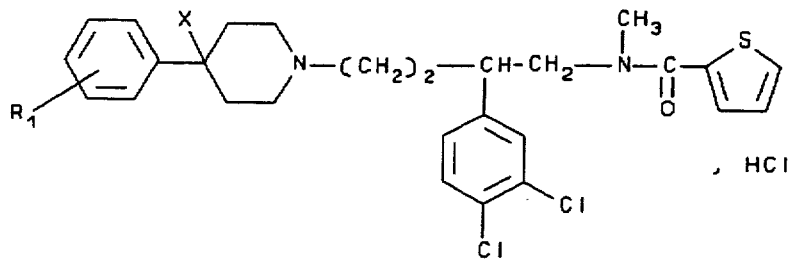

UNITED STATES PATENT AND TRADEMARK OFFICE
CERTIFICATE OF CORRECTION

PATENT NO. : 5,236,921

DATED : August 17, 1993

INVENTOR(S) : Emonds-Alt et al.

Page 8 of 10

It is certified that error appears in the above-indentified patent and that said Letters Patent is hereby corrected as shown below:

Column 35, the formula at the top of Table 8 should read as follows:

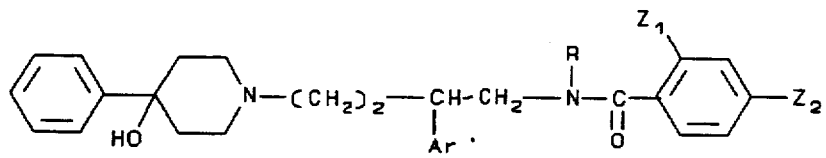

Column 37, the formula at the top of Table 9 should read as follows:

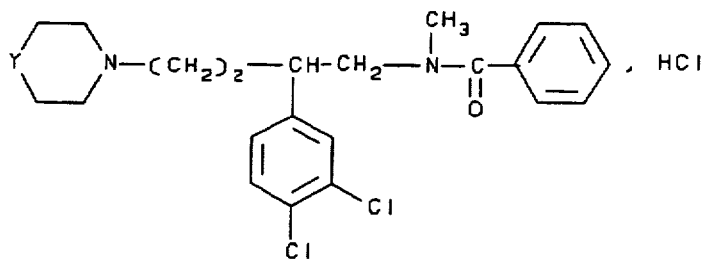

Column 38, the formula at the top of Table 9-continued should read as follows:

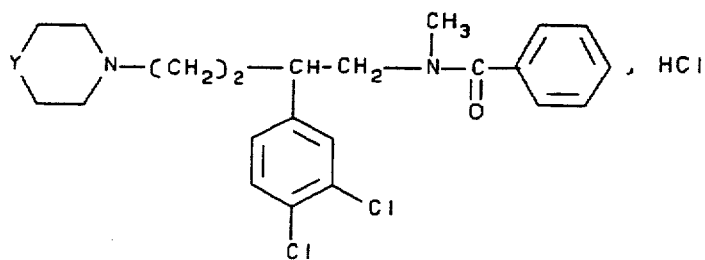

UNITED STATES PATENT AND TRADEMARK OFFICE
CERTIFICATE OF CORRECTION

PATENT NO. : 5,236,921
DATED : August 17, 1993
INVENTOR(S) : Emonds-Alt et al.

It is certified that error appears in the above-identified patent and that said Letters Patent is hereby corrected as shown below:

Column 39, the formula at the top of Table 10 should read as follows:

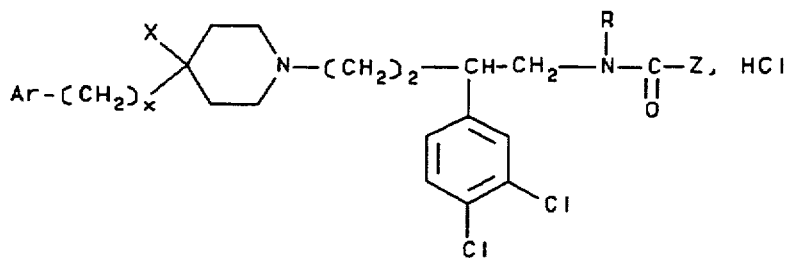

the formula for the

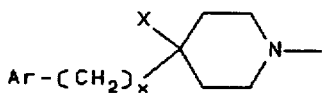

group of Example 68 should read as follows:

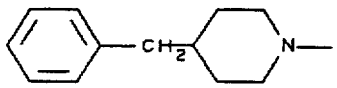

UNITED STATES PATENT AND TRADEMARK OFFICE
CERTIFICATE OF CORRECTION

PATENT NO. : 5,236,921
DATED : August 17, 1993
INVENTOR(S) : Emonds-Alt et al.

It is certified that error appears in the above-indentified patent and that said Letters Patent is hereby corrected as shown below:

the formula for the Z group of Example 68 should read as follows:

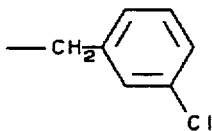

the formula for the Z group of Example 69 should read as follows:

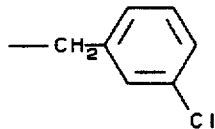

Signed and Sealed this

Twenty-eight Day of February, 1995

Attest:

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,236,921
DATED : August 17, 1993
INVENTOR(S) : Emonds-Ai et al.

It is certified that error appears in the above-identified patent and that said Letters Patent is hereby corrected as shown below:

<u>Column 45</u>,
Line 30, after "thienyl group," insert -- said phenyl group being --.

Signed and Sealed this

Fourteenth Day of May, 2002

*Attest:*

*Attesting Officer*

JAMES E. ROGAN
*Director of the United States Patent and Trademark Office*